United States Patent
Azzawi et al.

(10) Patent No.: US 10,633,697 B2
(45) Date of Patent: Apr. 28, 2020

(54) CAUTION CHELATOR HOT START

(71) Applicant: Qiagen GmbH, Hilden (DE)

(72) Inventors: Alexander Azzawi, Solingen (DE); Ralf Peist, Hilden (DE)

(73) Assignee: Qiagen GmbH, Hilden (DE)

( * ) Notice: Subject to any disclaimer, the term of this patent is extended or adjusted under 35 U.S.C. 154(b) by 193 days.

(21) Appl. No.: 15/114,787

(22) PCT Filed: Jan. 15, 2015

(86) PCT No.: PCT/EP2015/050671
§ 371 (c)(1),
(2) Date: Jul. 27, 2016

(87) PCT Pub. No.: WO2015/113828
PCT Pub. Date: Aug. 6, 2015

(65) Prior Publication Data
US 2016/0340712 A1 Nov. 24, 2016

(30) Foreign Application Priority Data
Jan. 31, 2014 (EP) .................... 14153386

(51) Int. Cl.
*C12Q 1/686* (2018.01)
*C12N 9/22* (2006.01)
*C12N 9/12* (2006.01)

(52) U.S. Cl.
CPC ........... *C12Q 1/686* (2013.01); *C12N 9/1241* (2013.01); *C12N 9/22* (2013.01); *C12Y 207/00* (2013.01); *C12Y 301/00* (2013.01)

(58) Field of Classification Search
None
See application file for complete search history.

(56) References Cited

U.S. PATENT DOCUMENTS

| 2003/0082567 A1 | 5/2003 | Barnes et al. |
| 2013/0330777 A1 | 12/2013 | Zhang et al. |

FOREIGN PATENT DOCUMENTS

| WO | 03/012066 A2 | 2/2003 |
| WO | 2006/008479 A1 | 1/2006 |
| WO | 2007/096182 A1 | 8/2007 |
| WO | 2013/068107 A1 | 5/2013 |

OTHER PUBLICATIONS

Kreader, C.A., "Relief of Amplification Inhibition in PCR with Bovine Serum Albumin or T4 Gene 32 Protein", Applied and Environmental Microbiology, Mar. 1996, vol. 62, No. 3, pp. 1102-1106.*

Arena et al., "Calcium- and Magnesium-EDTA complexes. Stability constants and their dependence on temperature and ionic strength," *Thermochimica Acta* 61(1-2):129-138, 1983.

Downey, "Interpreting melt curves: An indicator, not a diagnosis," Jan. 20, 2014, URL=http://eu.idtdna.com/pages/decoded/decoded-articles/core-concepts/decoded/2014/01/20/interpreting-melt-curves-an-indicator-not-a-diagnosis, download date Mar. 23, 2017, 9 pages.

Griko, "Energetics of $Ca^{2+}$-EDTA interactions: calorimetric study," *Biophysical Chemistry* 79(2):117-127, 1999.

Harrison et al., "Correction of proton and Ca association constants of EGTA for temperature and ionic strength," *American Journal of Physiology* 256(6):C1250-C1256, 1989.

Harrison et al., "The effect of temperature and ionic strength on the apparent Ca-affinity of EGTA and the analogous Ca-chelators BAPTA and dibromo-BAPTA," *Biochimica et Biophysica Acta* 925(2):133-143, 1987.

Huggett et al., "Differential susceptibility of PCR reactions to inhibitors: an important and unrecognised phenomenon," *BMC Research Notes* 1(1):70, 2008. (9 pages).

Price, "The Essential Role of $Ca^{2+}$ in the Activity of Bovine Pancreatic Deoxyribonuclease," *The Journal of Biological Chemistry* 250(6):1981-1986, 1975. (7 pages).

Al-Soud et al., "Capacity of Nine Thermostable DNA Polymerases to Mediate DNA Amplification in the Presence of PCR-Inhibiting Samples," *Applied and Environmental Microbiology* 64(10):3748-3753, 1998.

Jacobson et al., "Routine diagnostics of *Lawsonia intracellularis* performed by PCR, serological and post mortem examination, with special emphasis on sample preparation methods for PCR," *Veterinary Microbiology* 102:189-201, 2004.

\* cited by examiner

*Primary Examiner* — Suzanne M Noakes
(74) *Attorney, Agent, or Firm* — Seed IP Law Group LLP

(57) ABSTRACT

The invention is in the field of regulation of enzymatic activity in nucleic acid modifying reactions. It describes a method of regulating enzymatic activity by adding chelating agents to the reaction composition and exploits the fact that both the binding of divalent cations to these chelating agents and the pH of commonly used buffers is temperature dependent. PCR experiments that are hampered by non-specific side products can be regulated such that the target sequence is amplified in a more specific manner.

11 Claims, 19 Drawing Sheets

Specification includes a Sequence Listing.

Figure 4:
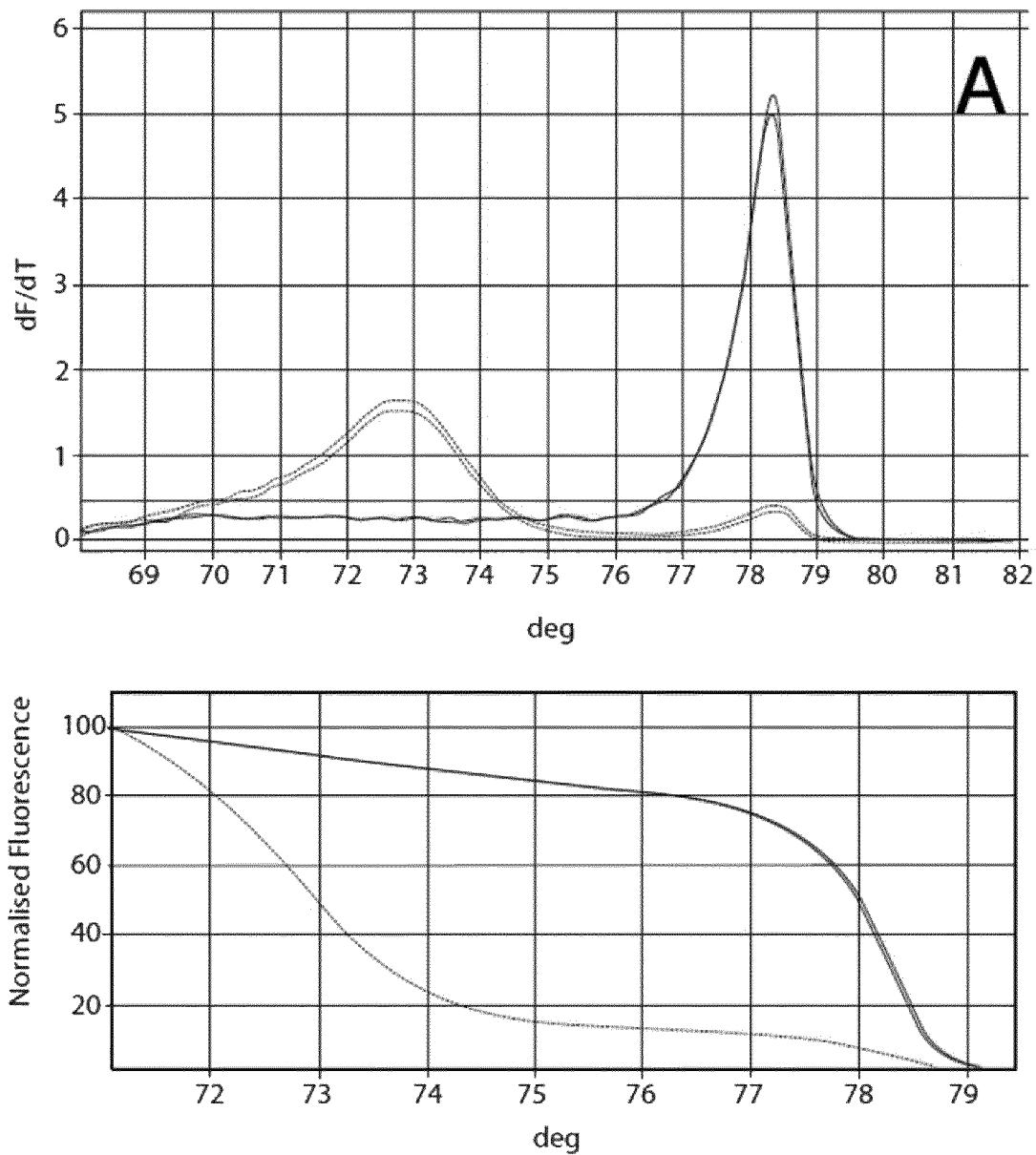
Figure 4:
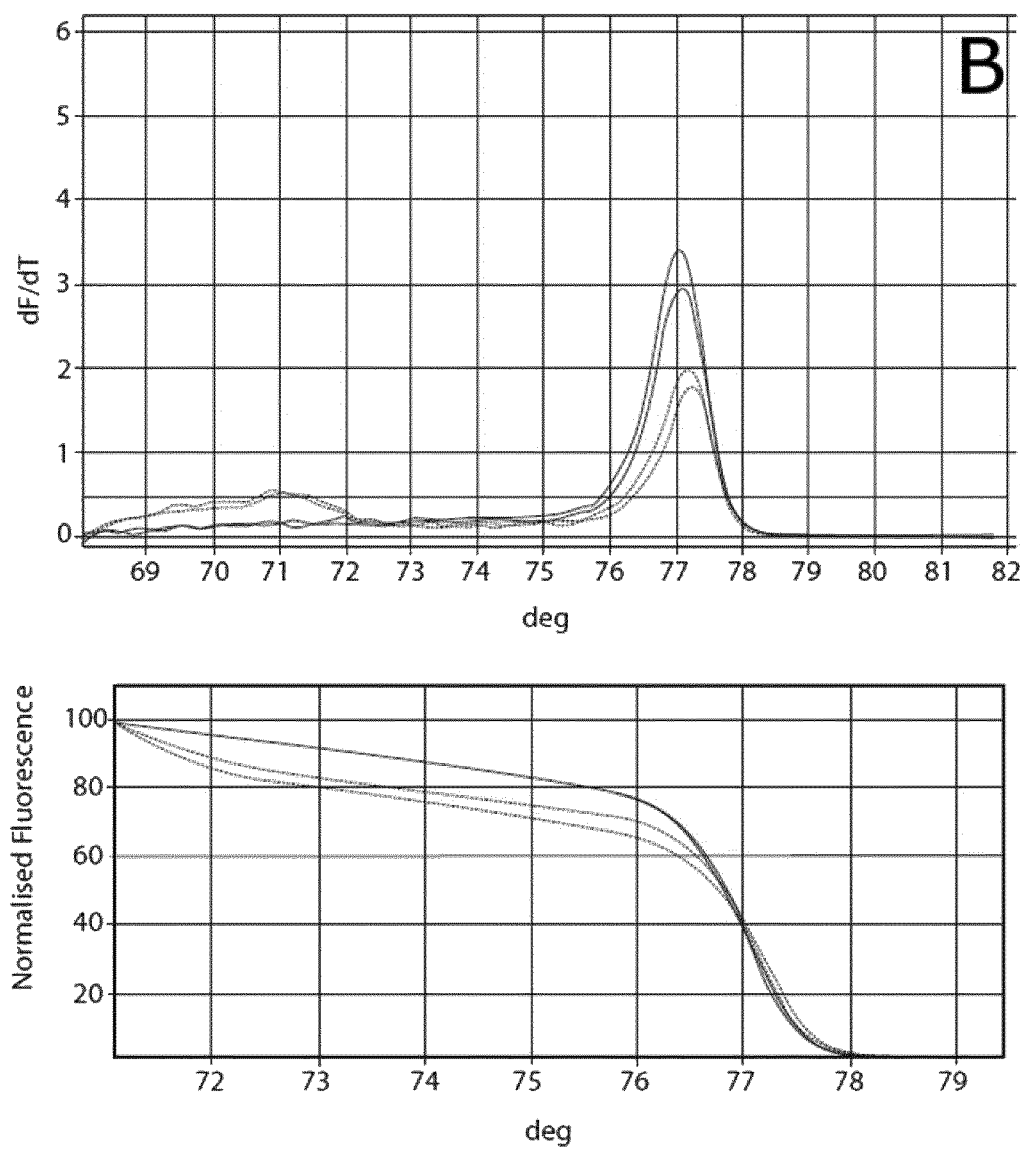
Figure 4:
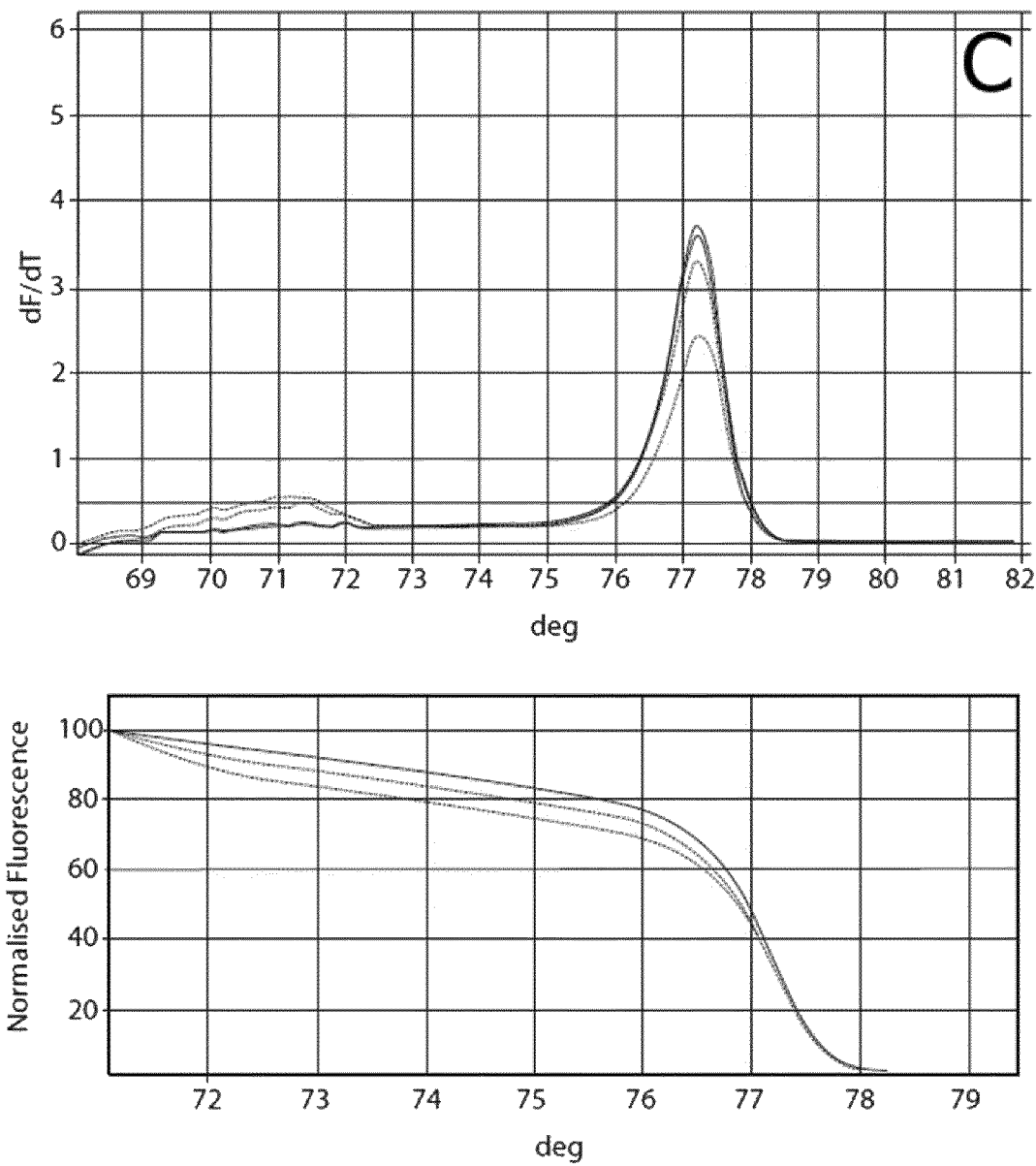
Figure 4:
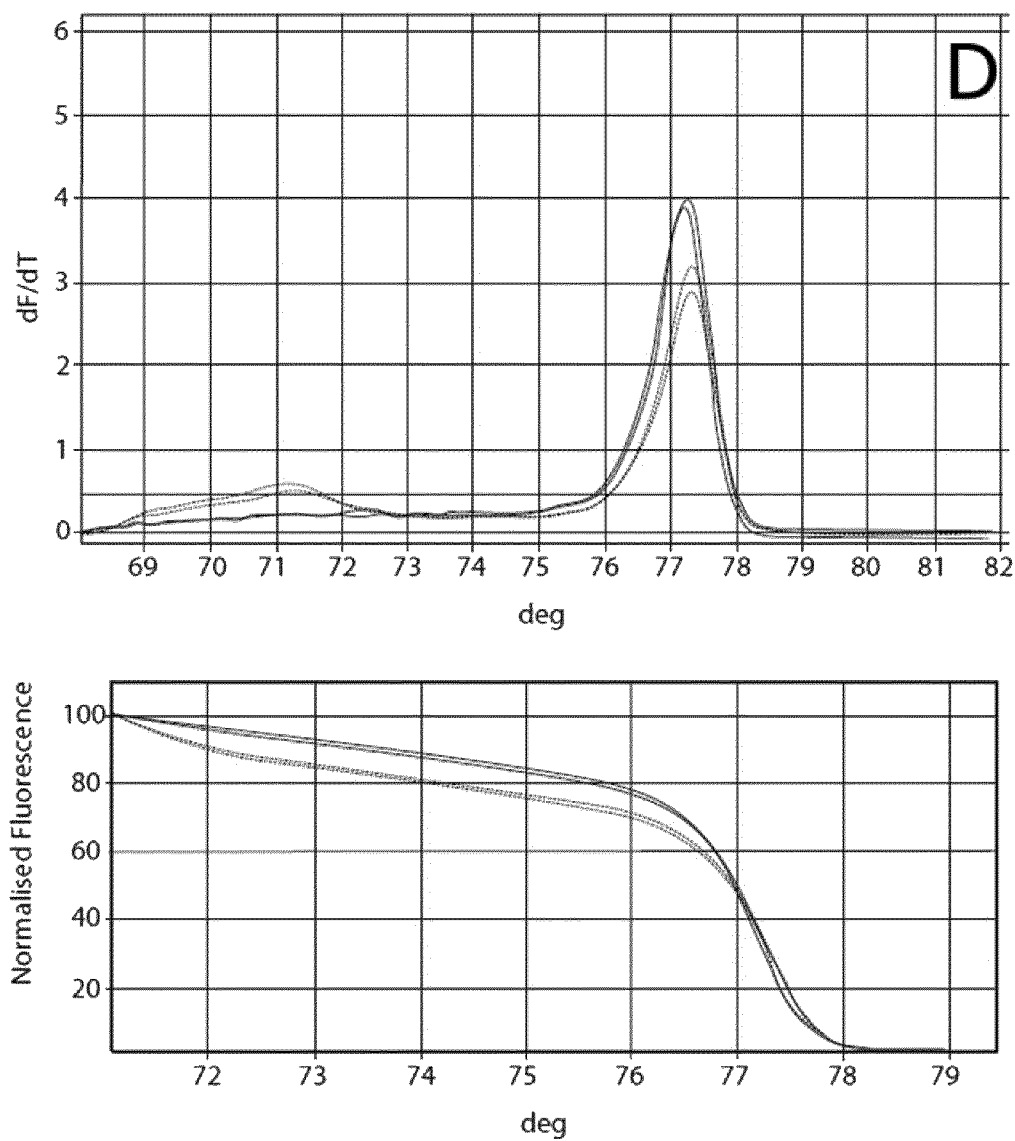
Figure 4:
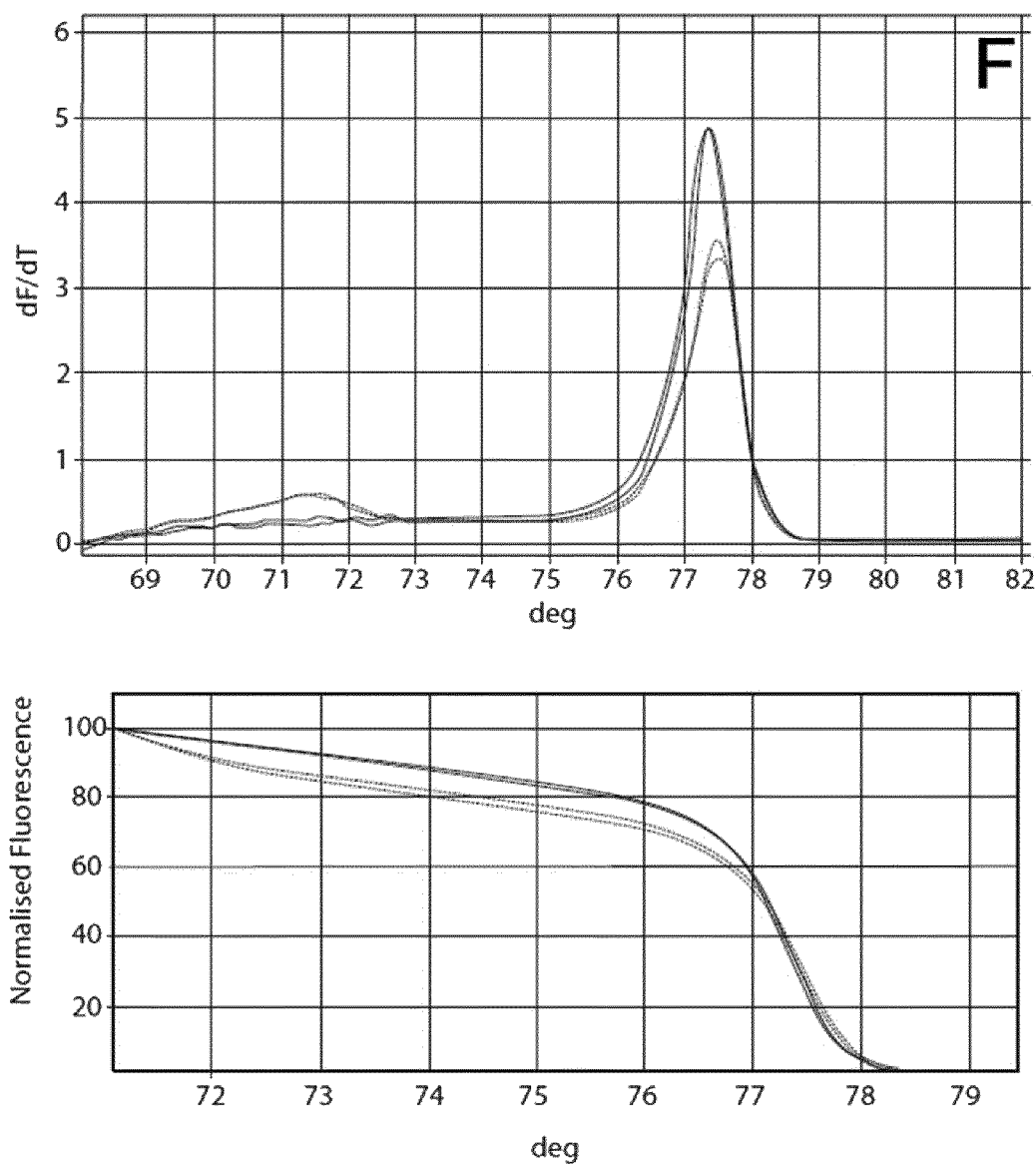
Figure 4:
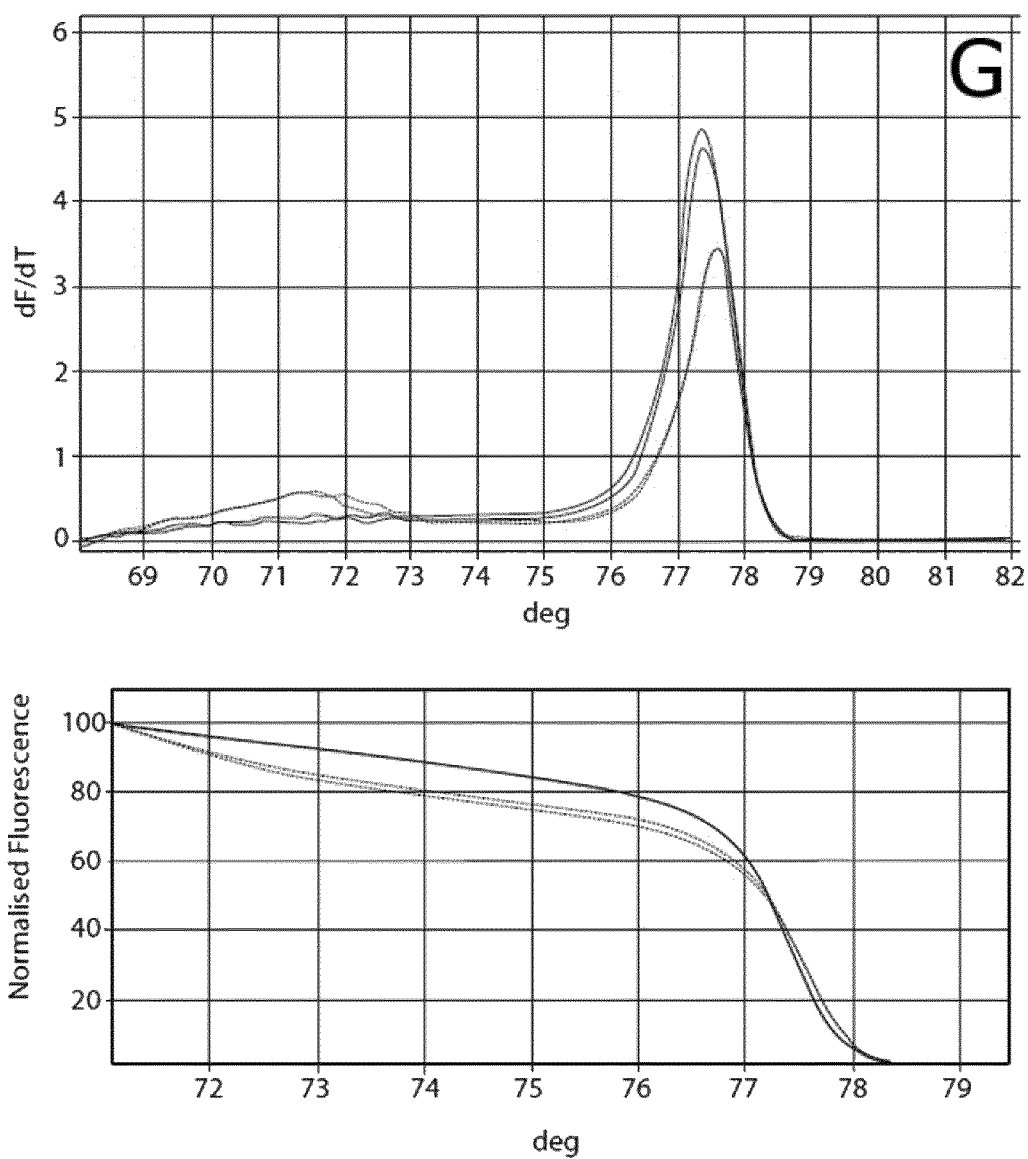
Figure 4:
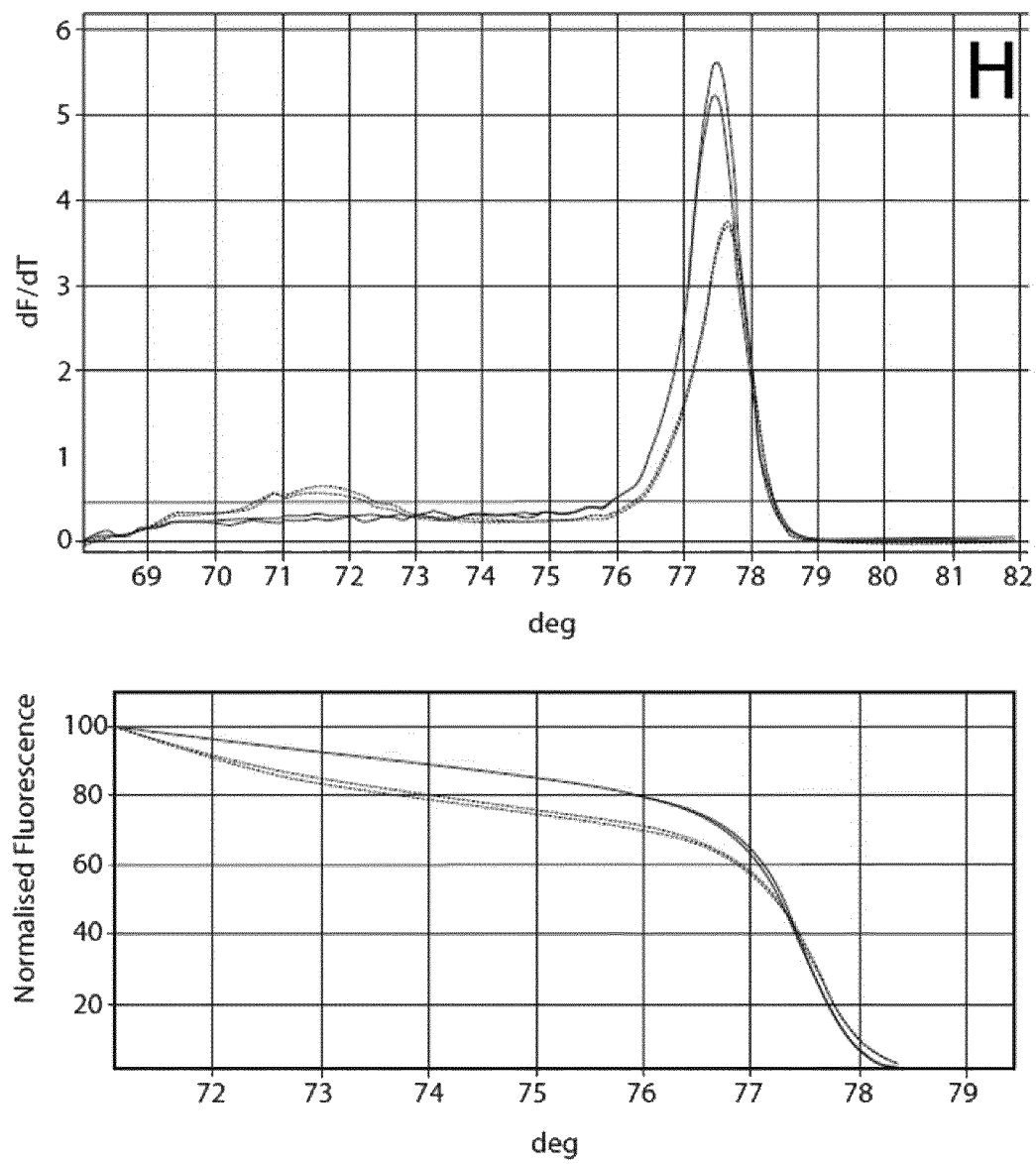

Figure 4 contiued
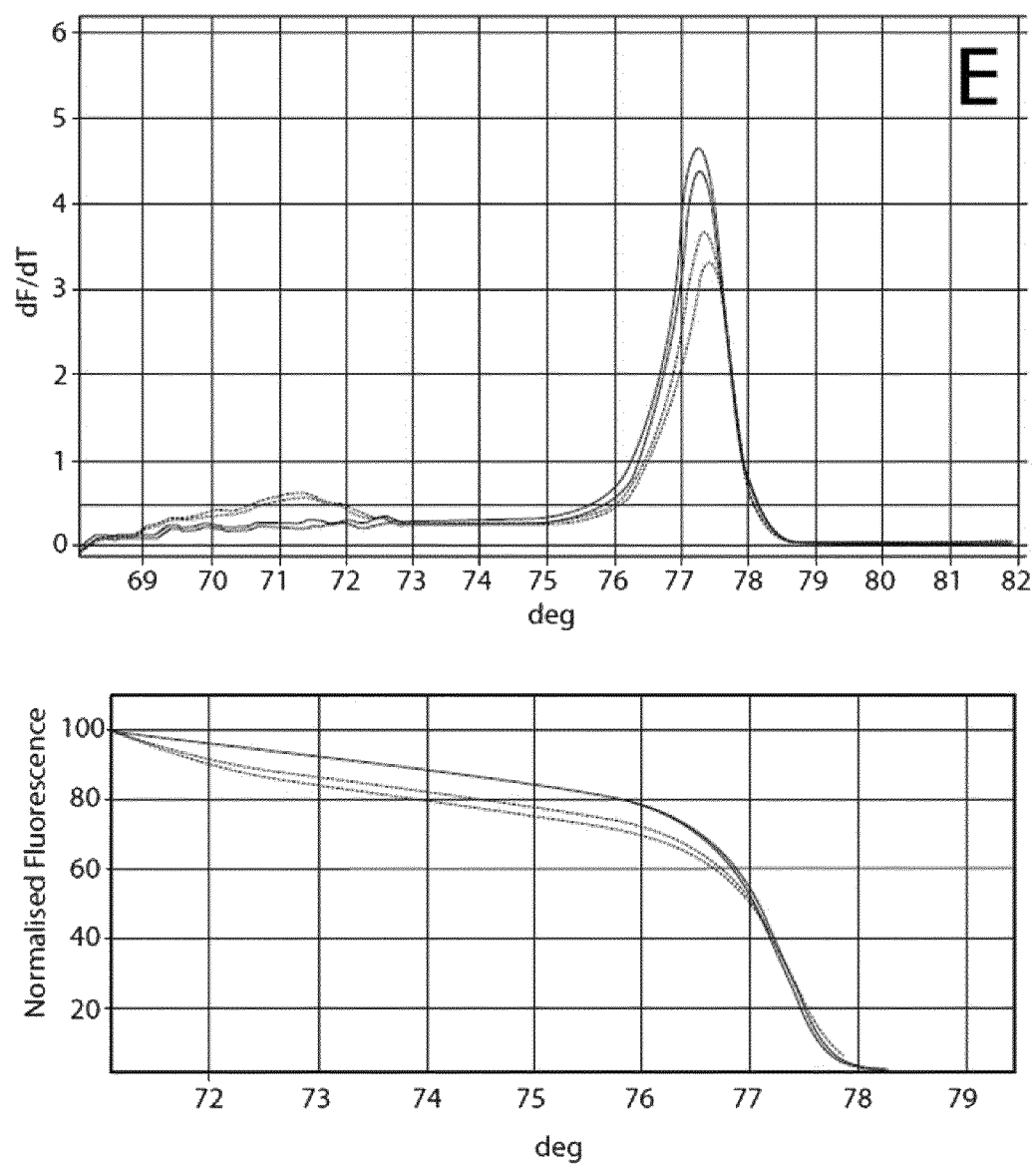

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: HugA Primer Sequence

<400> SEQUENCE: 1
cacacagcga tggcagctat gc                                          22

<210> SEQ ID NO 2
<211> LENGTH: 18
<212> TYPE: DNA
<213> ORGANISM: Artificial Sequence
<220> FEATURE:
<223> OTHER INFORMATION: HugB Primer Sequence

<400> SEQUENCE: 2
cccagtgatg ggccagct                                               18

<210> SEQ ID NO 3
<211> LENGTH: 26
<212> TYPE: DNA
<213> ORGANISM: Artificial Sequence
<220> FEATURE:
<223> OTHER INFORMATION: Primer Sequence Number 1

<400> SEQUENCE: 3
acccccacta aacataccct tattct                                      26

<210> SEQ ID NO 4
<211> LENGTH: 26
<212> TYPE: DNA
<213> ORGANISM: Artificial Sequence
<220> FEATURE:
<223> OTHER INFORMATION: Primer Sequence Number 2

<400> SEQUENCE: 4
gggagggtaa tgaagttgag tttagg                                      26
```

CAUTION CHELATOR HOT START

FIELD OF THE INVENTION

The present invention relates to the field of nucleic acid chemistry. More particular, it relates to the regulation of enzyme activity in the field of nucleic acid modifying reactions.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025.469USPCUSPC_SEQUENCE_LISTING.txt. The text file is 1.2 KB, was created on Jul. 27, 2016, and is being submitted electronically via EFS-Web.

BACKGROUND

Nucleic acid modifying reactions play a pivotal role in modern biological and pharmaceutical research, both in the academic and industrial settings. Such reactions cover a wide range of applications, ranging from nucleic acid amplification reactions to regulated and specific cleavage of nucleic acids. These are mediated by enzymes that have been studied extensively for the past decades.

Amplification of target nucleic acid sequences is of importance to modern biological and pharmaceutical industry. Large-scale robotic facilities used in industrial research depend on the accurate and efficient regulation of amplification conditions to ensure that the target sequences are correctly amplified for downstream applications.

Regulation of the activity of such enzymes is however not a trivial task. In the case of polymerases, efficient amplification is dependent on a complex interplay of parameters such as primer length, GC content of both primer and target sequences as well as ionic strength and composition of the reaction buffer. Further, non-specific binding of primers is often observed at lower temperatures during the amplification cycles. This increases the fraction of non-specific side products and lowers the overall efficiency of the amplification reaction.

To address this, recent developments in the field of polymerases describe "Hot Start" polymerases. This class of enzymes is either chemically inactivated or has the active site blocked due to binding of a specific antibody or an aptamer. After an activation step at high temperature, the chemical modification is cleaved off and the enzyme is activated.

In addition to "Hot Start" polymerases, so called "Hot Start" primers and "Hot Start" nucleotides have also been developed. These are chemically modified primers, wherein the modification is cleaved off at high temperatures and thus the primer is rendered functional and is able to hybridize to its target sequence. However, synthesis of such primers is expensive and requires more time than standard primers. Both in the case of the "Hot Start" primer and polymerases, the blocking features are only available once since the heat-induced removal of the chemical modification is irreversible.

There is a need for methods that allow for the regulation of enzymatic activity without elaborate modification of enzymes and substrates.

BRIEF DESCRIPTION OF THE INVENTION

The present invention relates to a method of regulation of enzymatic activity by controlling the concentration of divalent cations in the reaction composition.

The reaction composition comprises at least one enzyme, wherein the activity of said enzyme is dependent on divalent cations; a chelating agent; a divalent cation, wherein the binding of said cation to said chelating agent is dependent on pH and/or temperature of the reaction composition; a buffering system, wherein the acid dissociation constant is temperature dependent, such that a change in temperature results in a change of pH of the aqueous solution; and a substrate of said enzyme. In addition, changing the temperature in the reaction composition results in divalent cations which are bound to chelating agents being released from these complexes and thereby the enzyme is activated or increases activity. Chelating said cation does not have structural consequences; selectively complexing said cation modulates activity. The change in activity is reversible; inactivation by chelating can be reversed by releasing said cation upon temperature increase.

The invention also relates to a kit for performing a nucleic acid modifying reaction and comprises a buffer system, a chelating agent, a nucleic acid modifying enzyme and a divalent cation for said enzyme.

DETAILED DESCRIPTION OF THE INVENTION

The present invention relates to a method for the regulation of enzyme activity in a reaction composition. The reaction composition comprises at least one enzyme, wherein the activity of said enzyme is dependent on divalent cations; a chelating agent; a divalent cation, wherein the binding of said cation to said chelating agent is dependent on pH and/or temperature of the reaction composition; a buffering system, wherein the acid dissociation constant is temperature dependent, such that a change in temperature results in a change of pH of the aqueous solution; and a substrate of said enzyme. In addition, changing the temperature in the reaction composition results in divalent cations which are bound to chelating agents being released from these complexes and thereby the enzyme is activated or increases activity. Chelating said cation does not have structural consequences; selectively complexing said cation modulates activity. The change in activity is reversible; inactivation by chelating can be reversed by releasing said cation upon temperature increase.

In a preferred embodiment, the present invention relates to a method for the regulation of enzyme activity in a reaction composition. The reaction composition comprises at least one enzyme, wherein the activity of said enzyme is dependent on divalent cations; a chelating agent; a divalent cation, wherein the binding of said cation to said chelating agent is dependent on pH of the reaction composition; a buffering system, wherein the acid dissociation constant is temperature dependent, such that a change in temperature results in a change of pH of the aqueous solution; and a substrate of said enzyme. In addition, changing the temperature in the reaction composition results in divalent cations which are bound to chelating agents being released from these complexes and thereby the enzyme is activated or increases activity. Chelating said cation does not have structural consequences; selectively complexing said cation modulates activity. The change in activity is reversible;

inactivation by chelating can be reversed by releasing said cation upon temperature increase.

In one embodiment of the invention the enzyme is a nucleic acid modifying enzyme.

In one embodiment, the activity of the nucleic acid modifying enzyme comprises substrate binding and substrate processing activity.

In a preferred embodiment the nucleic acid modifying enzyme is selected from the group of polymerases, transcriptases and cation-dependent nucleases.

In a more preferred embodiment the polymerase is selected from the group of organisms comprising *Thermus, Aquifex, Thermotoga, Thermocridis, Hydrogenobacter, Thermosynchecoccus, Thermoanaerobacter, Pyrococcales, Thermococcus, Bacillus, Sulfolobus* and non-thermophiles. Preferably the viral reverse transcriptases are from MMLV, AMV HIV, EIAV and/or the nuclease is a bovine DNase.

In the most preferred embodiment the polymerase is selected from the group of organisms comprising *Aquifex aeolicus, Aquifex pyogenes, Thermus thermophilus, Thermus aquaticus, Thermotoga neopolitana, Thermus pacificus, Thermus eggertssonii* and *Thermotoga maritima*.

In particular, the invention also describes a method, wherein the removal of said divalent cation results in decreased or loss of activity of said nucleic acid modifying enzyme.

This represents an option to regulate enzymatic activity and substrate binding is at the level of the concentration of divalent cations in the reaction composition. For instance, in the case of polymerases and many nucleases, the concentration of divalent ions such as magnesium, calcium and others is crucial to the activity of the enzyme. A reduced level of said cations leads to vastly decreased activity or even abolishes enzymatic activity. In the case of polymerases, stability of hybridization of the primers to the target sequence is greatly reduced. Many nucleases possess a divalent cation in the active site that is crucial to substrate processing. A way to regulate enzymatic activity on the level of ion concentration exploits the fact that both the pH value of buffers routinely used in enzymatic reaction mixtures and the ability of chelating agents to bind ions is temperature-dependent. In addition to polymerases, other nucleic acid modifying enzymes such as nucleases also depend on divalent ions in their active site and therefore can be regulated as described above.

The invention also relates to a method, wherein the activity of said nucleic acid modifying enzyme is selected from the group comprising amplification, reverse transcription, isothermal amplification, sequencing and hydrolytic cleavage of ester bonds, preferably amplification, reverse transcription, and hydrolytic cleavage of ester bonds.

In a preferred embodiment of the invention the chelating agent is selected from the group comprising ethylene di amine tetra acetic acid (EDTA), ethylene glycol bis(amino ethyl) N,N'-tetra acetic acid and nitrile acetic acid (NTA). Particularly preferred is EGTA.

In one embodiment the divalent cation is selected from the group comprising $Mg^{2+}$, $Ca^{2+}$, $Mn^{2+}$, $Cu^{2+}$, $Fe^{2+}$, $Ni^{2+}$, $Zn^{2+}$ and $Co^{2+}$. In a preferred embodiment, the chelating agent is EDTA and the cations are selected from $Mg^{2+}$, $Ca^{2+}$, $Mn^{2+}$, $Cu^{2+}$, $Ni^{2+}$, $Zn^{2+}$ and/or $Co^{2+}$.

In one embodiment, several cations selected from the group comprising $Mg^{2+}$, $Ca^{2+}$, $Mn^{2+}$, $Cu^{2+}$, $Fe^{2+}$, $Ni^{2+}$, $Zn^{2+}$ and $Co^{2+}$ are present in the reaction.

In one embodiment the chelating agent is EGTA and the cations are $Ca^{2+}$ and/or $Mg^{2+}$.

In one embodiment the chelating agent is NTA and the cations are $Ca^{2+}$ and/or $Cu^{2+}$ and/or $Co^{2+}$.

In another embodiment of the invention the buffer is suitable for enzymatic reactions. Preferably the buffer is selected from Table 4. Tris buffer is used in enzymatic reactions, preferably in PCR experiments. The pH value of Tris buffer is temperature dependent. At room temperature, the pH is around 8.7. A shift in pH of 0.03 pH units per ° C. is observed. Therefore, at 95° C. the pH is 6.6.

In one embodiment, the concentration of the buffer system is between 0.01 and 100 mM, preferably between 0.1 and 50 mM, more preferably between 1 and 30 mM and most preferably between 5 and 15 mM.

In one embodiment, the concentration of the divalent cation in the reaction is between 0.01 and 20 mM, preferably between 0.1 and 10 mM, most preferable between 1 and 8 mM.

In one embodiment, the concentration of the chelating agent is between 0.05 and 50 mM, more preferably between 0.1 and 20 mM, even more preferably between 0.5 and 10 mM, and most preferably between 1 and 8 mM.

In one embodiment, the pH varies during the reaction in response to the temperature change by at least 0.05 pH units, preferably by at least 0.1, more preferably by at least 0.5, even more preferably by at least 1 and most preferably by at least 2 pH units.

The invention relates to a method, wherein the reaction composition comprises a buffer system, preferably a Tris buffer system, wherein the divalent cation is $Mg^{2+}$, preferably at a concentration between 0.01 and 20 mM; wherein the chelating agent is EGTA at a concentration between 0.05 and 50 mM and wherein the nucleic acid modifying enzyme is a DNA polymerase, preferably a hot start polymerase. Preferred EGTA concentration is between 0.1 mM and 20 mM, more preferred between 0.5 mM and 10 mM.

The invention also relates to a method, wherein the reaction composition comprises a buffer system, preferably a Tris buffer system; wherein the divalent cation is selected from the group of $Mg^{2+}$, $Ca^{2+}$, $Mn^{2+}$, $Cu^{2+}$, $Fe^{2+}$, $Ni^{2+}$, $Zn^{2+}$ and $Co^{2+}$; wherein the chelating agent is selected from the group of EGTA, EDTA and NTA and wherein the nucleic acid enzyme is a nuclease.

Further, the invention relates to a kit for performing a nucleic acid modifying reaction comprising a buffer system, a chelating agent, a nucleic acid modifying enzyme and a divalent cation for said enzyme.

EXAMPLES

Selection of Chelating Agent

Figure 1:
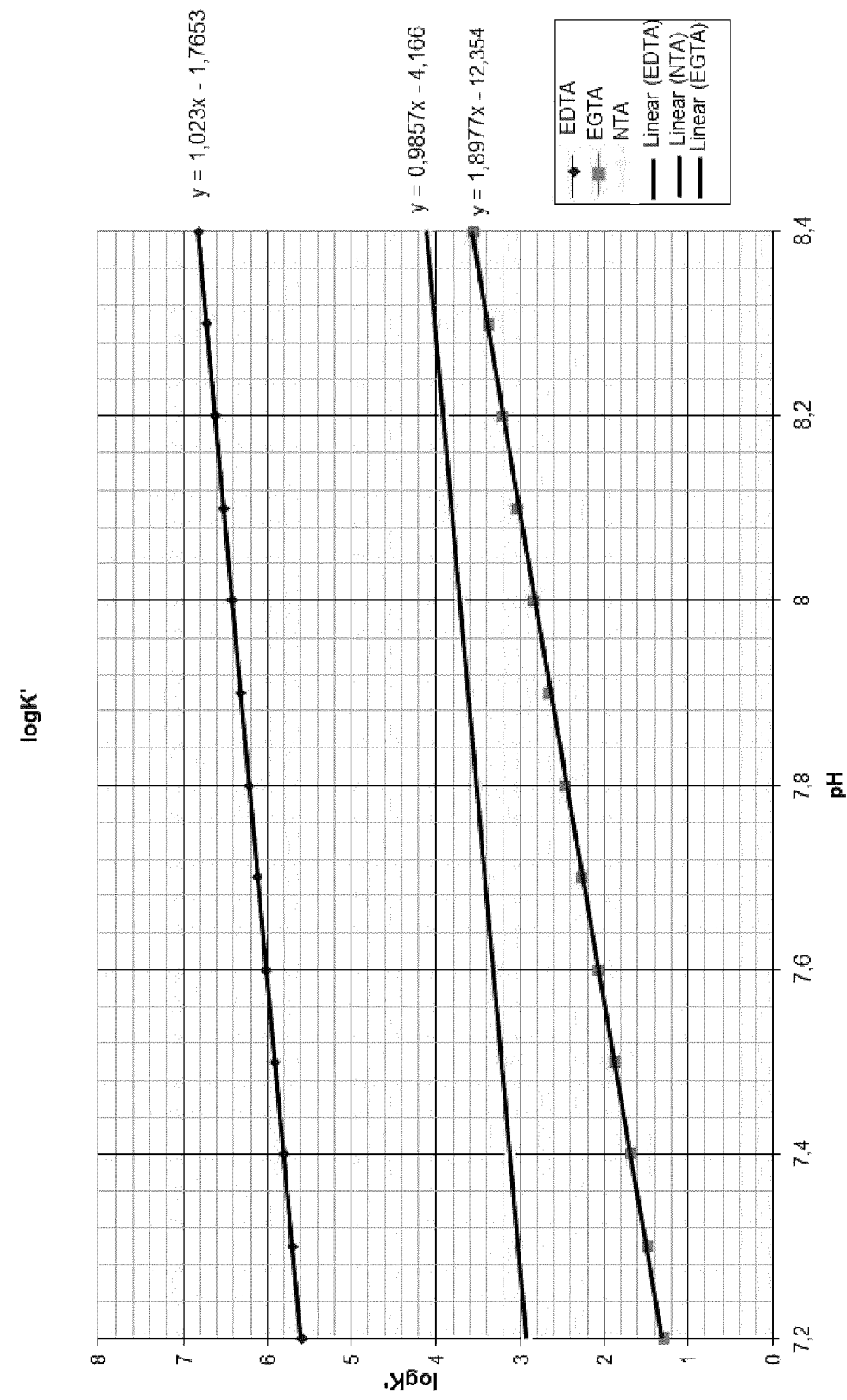

Tris buffer is routinely used in PCR buffers. At room temperature the pH of a Tris based PCR buffer is 8.7. Tris shows a temperature-dependent shift in pH value of 0.03 pH units per ° C. This means that at 95° C. the pH value is 6.6. In order to select a chelating agent for PCR experiments, the pH-dependency of the binding constants of three different chelating agents, NTA; EDTA and EGTA, was investigated. Known pK values from literature for every chelating agent were used to determine the pH dependency of the complex formation (FIG. 1). The correlation curve for EGTA shows a strong correlation between pH value and binding constant. Therefore, EGTA was selected for subsequent experiments.

Endpoint PCR

An amplification experiment was performed using a test system that is known to be prone to produce non-specific side products. A genomic DNA sequence of 1.2 kb was the target sequence. Primers HugA and HugB were used.

The primer sequences are as follows:

TABLE 1

Primer sequences used for endpoint PCR experiment.

| SEQ ID NO | Primer name | Sequence |
|---|---|---|
| 1 | HugA | CACACAGCGATGGCAGCTATGC |
| 2 | HugB | CCCAGTGATGGGCCAGCT |

Reactions with and without EGTA were performed in parallel. In set A, the magnesium concentration was varied in 1 mM steps, start and end point were 5 and 10 mM respectively. In set B, the start point was 0.5 mM and the end point was 4 mM Mg. The setup is described in Table 2.

TABLE 2

HugI PCR reactions mixture.

| | MM A | MM B | |
|---|---|---|---|
| Puffer (—Mg) | 1 | 1 | X |
| Taq | 0.625 | 0.625 | Units |
| Primer HugA | 0.5 | 0.5 | µM |
| Primer HugB | 0.5 | 0.5 | µM |
| dNTPs | 0.2 | 0.2 | mM |
| gDNA | 10 | 10 | ng |
| EGTA | 5 | 0 | mM |

The amplification program was as follows (Table 3):

TABLE 3

Amplification program of HugI PCR.

| Time [min:sec] | Temp [° C.] |
|---|---|
| 03:00 | 95 |
| 00:30 | 94 |
| 01:00 | 59 |
| 01:00 | 72 |
| 10:00 | 72 |
| | 4 |

35 cycles were performed.

The analysis of the PCR reactions on the agarose gel (FIG. 2) shows that the reactions containing EGTA as a chelating agent are more specific as of having less side products compared to those reactions without EGTA. Other buffers routinely used in enzymatic reactions are listed in Table 4.

TABLE 4

List of buffers commonly used in enzymatic reactions.

| Buffer ID No. | Product # | Description | Useful pH Range | CAS Number | pKa |
|---|---|---|---|---|---|
| 1 | A3594 | ACES BioPerformance Certified, ≥99.0% | 6.1-7.5 | 7365-82-4 | 6.80 |
| 2 | B4554 | BES BioPerformance Certified, cell culture tested, ≥99.0% | 6.4-7.8 | 10191-18-1 | 7.10 |
| 3 | B4429 | BIS-TRIS BioPerformance Certified, cell culture tested, suitable for insect cell culture, ≥98% | 5.8-7.2 | 6976-37-0 | 6.50 |
| 4 | B4679 | BIS-TRIS propane BioPerformance Certified, cell culture tested, ≥99.0% | 6.3-9.5 | 64431-96-5 | 6.80 |
| 5 | E0276 | EPPS BioPerformance Certified, cell culture tested, ≥99.5% (titration) | 7.3-8.7 | 16052-06-5 | 8.00 |
| 6 | G3915 | Gly-Gly BioPerformance Certified, cell culture tested, ≥99% | 7.5-8.9 | 556-50-3 | 8.20 |
| 7 | H4034 | HEPES BioPerformance Certified, ≥99.5% (titration), cell culture tested | 6.8-8.2 | 7365-45-9 | 7.50 |
| 8 | H3784 | HEPES sodium salt BioPerformance Certified, suitable for cell culture, ≥99.5% | 6.8-8.2 | 75277-39-3 | 7.50 |
| 9 | H3662 | HEPES sodium salt solution 1M, BioReagent, suitable for cell culture | | 75277-39-3 | |
| 10 | H3537 | HEPES solution 1M, BioReagent, suitable for cell culture, suitable for molecular biology, 0.2 µm filtered | 6.8-8.2 | 7365-45-9 | |
| 11 | M2933 | MES hydrate BioPerformance Certified, suitable for cell culture, ≥99.5% | 5.5-6.7 | 4432-31-9 (anhydrous) | 6.10 |
| 12 | M3058 | MES sodium salt BioPerformance Certified, suitable for cell culture | 5.5-6.7 | 71119-23-8 | 6.10 |
| 13 | M1317 | MES solution 1M, BioReagent, for molecular biology, suitable for cell culture | 5.5-6.7 | | |
| 14 | M3183 | MOPS BioPerformance Certified, cell culture tested, ≥99.5% (titration) | 6.5-7.9 | 1132-61-2 | 7.20 |
| 15 | M9024 | MOPS sodium salt BioPerformance Certified, suitable for cell culture, ≥99.5% | 6.5-7.9 | 71119-22-7 | 7.20 |
| 16 | M1442 | MOPS solution BioReagent, 1M, for molecular biology, suitable for cell culture | 6.5-7.9 | | |
| 17 | P1851 | PIPES BioPerformance Certified, suitable for cell culture, ≥99% | 6.1-7.5 | 5625-37-6 | 6.80 |
| 18 | P5493 | Phosphate buffered saline 10× concentrate, BioPerformance Certified, suitable for cell culture | | | |

TABLE 4-continued

List of buffers commonly used in enzymatic reactions.

| Buffer ID No. | Product # | Description | Useful pH Range | CAS Number | pKa |
|---|---|---|---|---|---|
| 19 | P5368 | Phosphate buffered saline BioPerformance Certified, pH 7.4 | | | |
| 20 | S6191 | Sodium chloride BioPerformance Certified, ≥99.5% (titration), Cell Culture Tested | | 7647-14-5 | |
| 21 | S6566 | Sodium phosphate monobasic Biotechnology Performance Certified, Cell Culture Tested | | 7558-80-7 | |
| 22 | T5316 | TAPS BioPerformance Certified, cell culture tested, ≥99.5% (titration) | 7.7-9.1 | 29915-38-6 | 8.40 |
| 23 | T5441 | TAPS sodium salt BioPerformance Certified, suitable for cell culture, ≥99% | 7.7-9.1 | 91000-53-2 | 8.40 |
| 24 | T5691 | TES BioPerformance Certified, cell culture tested, ≥99% (titration) | 6.8-8.2 | 7365-44-8 | 7.50 |
| 25 | T5816 | Tricine BioPerformance Certified, cell culture tested, ≥99% (titration) | 7.4-8.8 | 1389475.00 | 8.10 |
| 26 | T7193 | Trizma ® Pre-set crystals BioPerformance Certified, pH 7.0, average Mw 154.8 | 7.0-9.0 | | |
| 27 | T9943 | Trizma ® Pre-set crystals BioPerformance Certified, pH 7.0, average Mw 154.8 | 7.0-9.0 | | |
| 28 | T7443 | Trizma ® Pre-set crystals BioPerformance Certified, pH 7.2, average Mw 153.8 | 7.0-9.0 | | |
| 29 | T7693 | Trizma ® Pre-set crystals BioPerformance Certified, pH 7.4, average Mw 151.6 | 7.0-9.0 | | |
| 30 | T0319 | Trizma ® Pre-set crystals BioPerformance Certified, pH 7.4, average Mw 151.6 | 7.0-9.0 | | |
| 31 | T7818 | Trizma ® Pre-set crystals BioPerformance Certified, pH 7.5, average Mw 150.6 | 7.0-9.0 | | |
| 32 | T7943 | Trizma ® Pre-set crystals BioPerformance Certified, pH 7.6, average Mw 149.0 | 7.0-9.0 | | |
| 33 | T8068 | Trizma ® Pre-set crystals BioPerformance Certified, pH 7.7, average Mw 147.6 | 7.0-9.0 | | |
| 34 | T8193 | Trizma ® Pre-set crystals BioPerformance Certified, pH 7.8, average Mw 145.8 | 7.0-9.0 | | |
| 35 | T8443 | Trizma ® Pre-set crystals BioPerformance Certified, pH 8.0, average Mw 141.8 | 7.0-9.0 | | |
| 36 | T0819 | Trizma ® Pre-set crystals BioPerformance Certified, pH 8.0, average Mw 141.8 | 7.0-9.0 | | |
| 37 | T8568 | Trizma ® Pre-set crystals BioPerformance Certified, pH 8.1, average Mw 139.8 | 7.0-9.0 | | |
| 38 | T8943 | Trizma ® Pre-set crystals BioPerformance Certified, pH 8.3, average Mw 135.4 | 7.0-9.0 | | |
| 39 | T8818 | Trizma ® Pre-set crystals BioPerformance Certified, pH 8.5, average Mw 131.4 | 7.0-9.0 | | |
| 40 | T1194 | Trizma ® Pre-set crystals BioPerformance Certified, pH 8.5, average Mw 131.4 | 7.0-9.0 | | |
| 41 | T9443 | Trizma ® Pre-set crystals BioPerformance Certified, pH 8.8, average Mw 127.2 | 7.0-9.0 | | |
| 42 | T9568 | Trizma ® Pre-set crystals BioPerformance Certified, pH 8.9, average Mw 125.6 | 7.0-9.0 | | |
| 43 | T9693 | Trizma ® Pre-set crystals BioPerformance Certified, pH 9.0, average Mw 124.6 | 7.0-9.0 | | |
| 44 | T1444 | Trizma ® Pre-set crystals BioPerformance Certified, pH 9.0, average Mw 124.6 | 7.0-9.0 | | |
| 45 | T9818 | Trizma ® Pre-set crystals BioPerformance Certified, pH 9.1, average Mw 123.0 | 7.0-9.0 | | |
| 46 | T0194 | Trizma ® Pre-set crystals pH 7.2, average Mw 153.8 | 7.0-9.0 | | |
| 47 | T0444 | Trizma ® Pre-set crystals pH 7.5, average Mw 150.6 | 7.0-9.0 | | |
| 48 | T0569 | Trizma ® Pre-set crystals pH 7.6, average Mw 149.0 | 7.0-9.0 | | |
| 49 | T0694 | Trizma ® Pre-set crystals pH 7.7, average Mw 147.6 | 7.0-9.0 | | |
| 50 | T0944 | Trizma ® Pre-set crystals pH 8.1, average Mw 139.8 | 7.0-9.0 | | |
| 51 | T1069 | Trizma ® Pre-set crystals pH 8.3, average Mw 135.4 | 7.0-9.0 | | |
| 52 | T1319 | Trizma ® Pre-set crystals pH 8.8, average Mw 127.2 | 7.0-9.0 | | |
| 53 | T6066 | Trizma ® base BioPerformance Certified, meets EP, USP testing specifications, cell culture tested, ≥99.9% (titration) | 41524.00 | 77-86-1 | 8.10 |
| 54 | T5941 | Trizma ® hydrochloride BioPerformance Certified, cell culture tested, ≥99.0% (titration) | 7.0-9.0 | 1185-53-1 | 8.10 |

TABLE 4-continued

List of buffers commonly used in enzymatic reactions.

| Buffer ID No. | Product # | Description | Useful pH Range | CAS Number | pKa |
|---|---|---|---|---|---|
| 55 | T1819 | Trizma ® hydrochloride solution pH 7.0, 1M, BioReagent, for molecular biology, suitable for cell culture | 7.0-9.0 | | |
| 56 | T2069 | Trizma ® hydrochloride solution pH 7.2, 1M, BioReagent, for molecular biology, suitable for cell culture | 7.0-9.0 | | |
| 57 | T1944 | Trizma ® hydrochloride solution pH 7.4, 0.1M | 7.0-9.0 | | |
| 58 | T2194 | Trizma ® hydrochloride solution pH 7.4, 1M, BioReagent, for molecular biology, suitable for cell culture | 7.0-9.0 | | |
| 59 | T2319 | Trizma ® hydrochloride solution pH 7.5, 1M, BioReagent, for molecular biology, suitable for cell culture | 7.0-9.0 | | |
| 60 | T2944 | Trizma ® hydrochloride solution pH 7.5, 2M, BioReagent, for molecular biology, suitable for cell culture | 7.0-9.0 | | |
| 61 | T2444 | Trizma ® hydrochloride solution pH 7.6, 1M, BioReagent, for molecular biology, suitable for cell culture | 7.0-9.0 | | |
| 62 | T2569 | Trizma ® hydrochloride solution pH 7.8, 1M, BioReagent, for molecular biology, suitable for cell culture | 7.0-9.0 | | |
| 63 | T2694 | Trizma ® hydrochloride solution pH 8.0, 1M, BioReagent, for molecular biology, suitable for cell culture | 7.0-9.0 | | |
| 64 | T3069 | Trizma ® hydrochloride solution pH 8.0, 2M, BioReagent, for molecular biology, suitable for cell culture | 7.0-9.0 | | |
| 65 | T2819 | Trizma ® hydrochloride solution pH 9.0, 1M, BioReagent, for molecular biology, suitable for cell culture | 7.0-9.0 | | |

Modulation of Residual Activity of Chemically Inactivated Taq DNA Polymerase Using EGTA/EDTA The following experiments employed a system to detect the formation of primer dimers in a PCR reaction mixture using residual active Taq polymerase molecules. Herein, bisulphite-treated DNA is used as a template. As a consequence of the bisulphite treatment, which entails the chemical modification of non-methylated cytosines to uracil), said template only consists of three bases. Since bisulphite treatment only works when using single stranded DNA, the majority of DNA after completion of said bisulphite treatment is single stranded. Primers that are used for amplification of such DNA sequences are characterized by reduced complexity since they only consist of three bases. Hence these primers are prone to dimer formation and are very likely to be able to bind >100.000 times to said bisulphite-treated DNA.

Genomic DNA was propagated using the Qiagen REPLI g Midi Kit according to the manufacturer's protocol. Subsequently, 1 μg of said genomic DNA was used in 10 independent reactions wherein the DNA was subjected to bisulphite treatment using the EpiTect Bisulfite Kit followed by purification. The resulting DNA of each reaction was pooled and used in the subsequent amplification reactions. Primer sequences are shown in Table 5.

TABLE 5

Primers used in amplification of bisulphite-treated DNA.

| SEQ ID NO | Primer NO | Sequence |
|---|---|---|
| 3 | 1 | ACCCCCACTAAACATACCCTTATTCT |
| 4 | 2 | GGGAGGGTAATGAAGTTGAGTTTAGG |

TABLE 6

Amplification reaction mixture.

| Reagent | Concentration | Volume (μl) |
|---|---|---|
| EpiTect HRM PCR Kit | 2x | 12.5 |
| Primer 1 | 10 μM | 1.875 |
| Primer 2 | 10 μM | 1.875 |
| Bisulphite-treated DNA | 10 ng/μl | 1 |
| Water or EGTA | 1-x mM | 5 |
| Water | | 2.75 |

The final EGTA concentration was between 0.25 and 10 mM.

One set of samples consisting of two reactions was incubated on ice for 120 min, whereas the other set of samples also consisting of two reactions was incubated at room temperature for 120 min. Subsequently both sets of samples were analyzed using the Rotor-Gene Q 5plex HRM System. The cycling program is shown in Table 7.

TABLE 7

Cycling program used in the amplification of bisulphite-treated DNA.

| 95° C. - 5' | |
|---|---|
| 95° C. - 10" | |
| 55° C. - 30" | x 40 |
| 72° C. - 10" | |
| HRM 68° C.-82° C. | |

Figure 3:
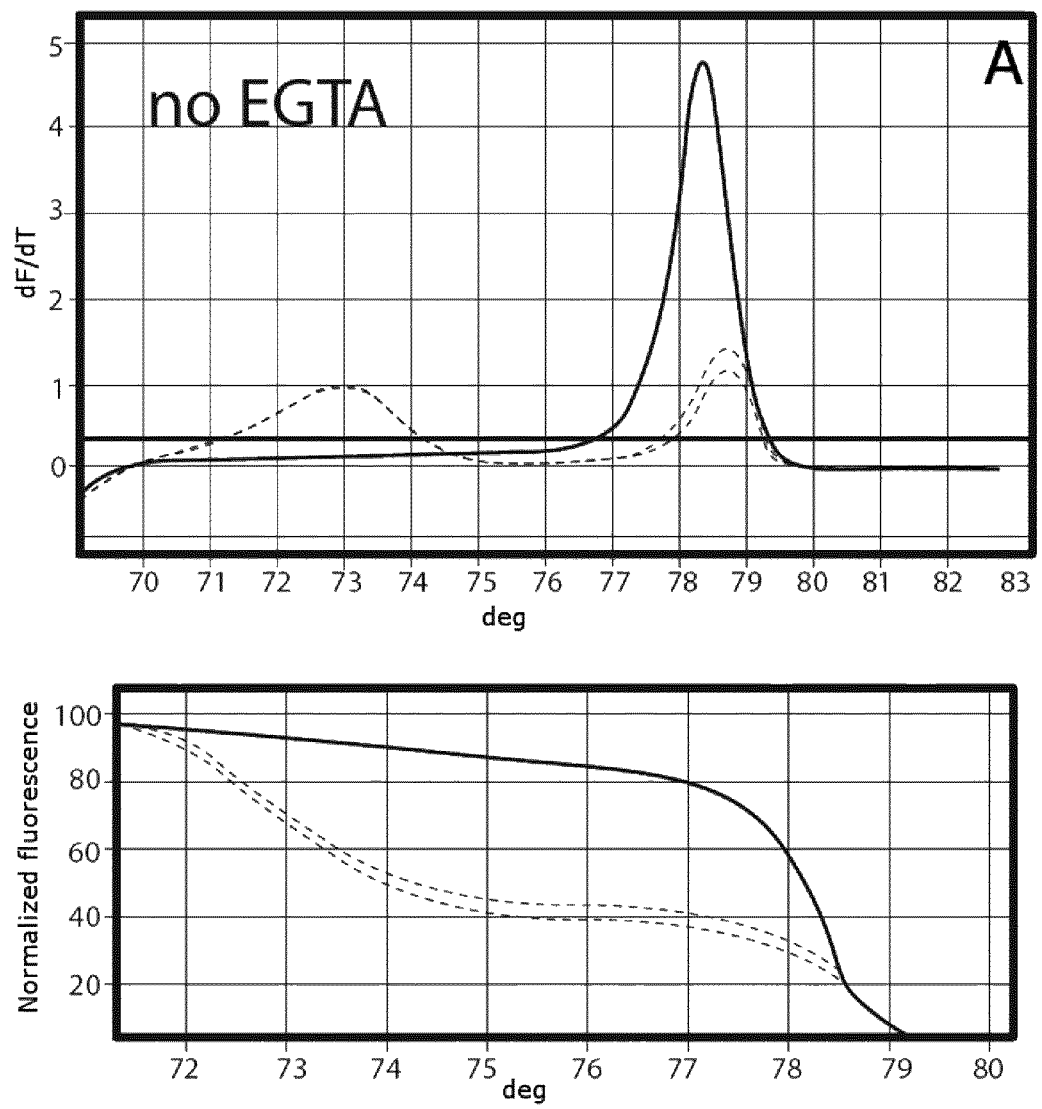
Figure 3:
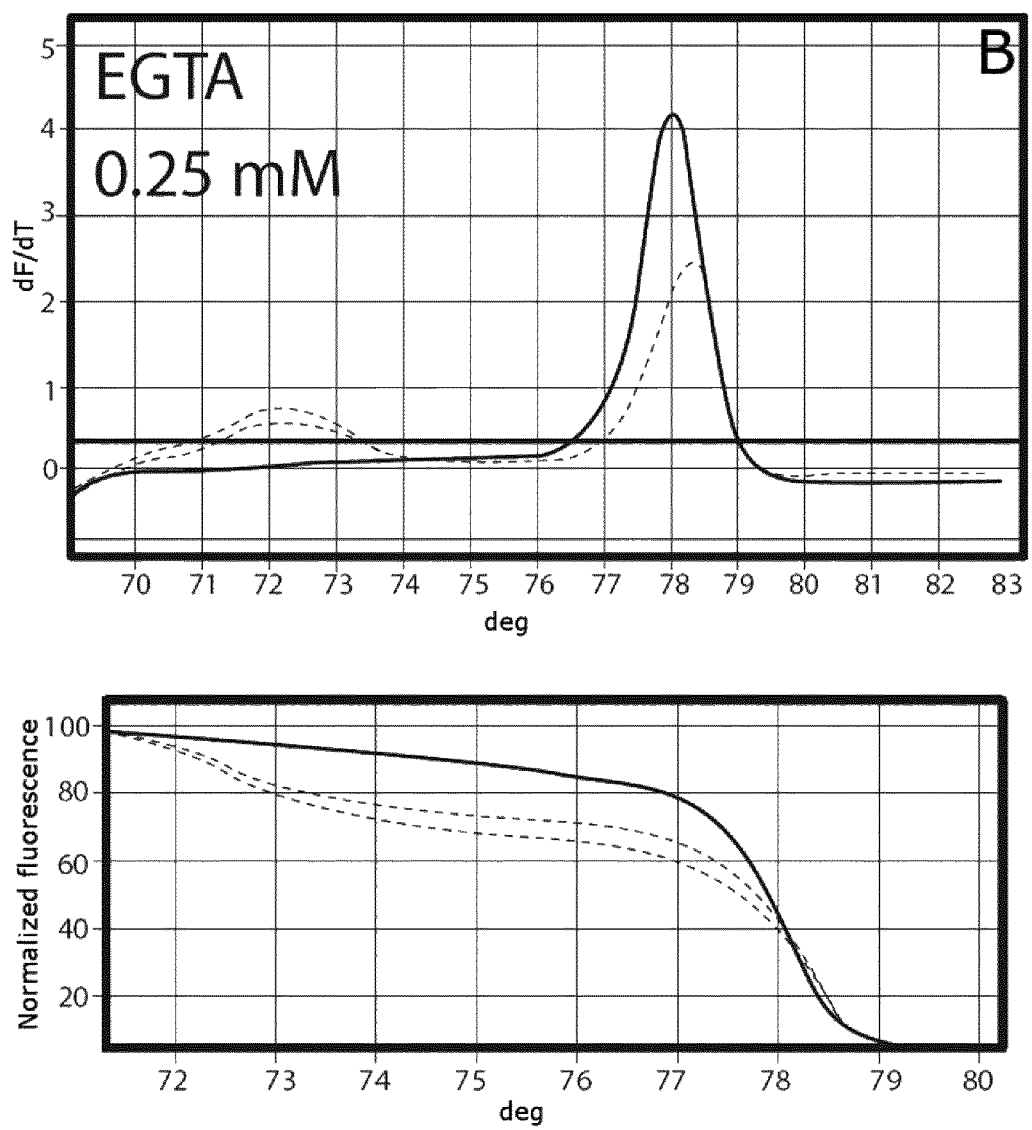
Figure 3:
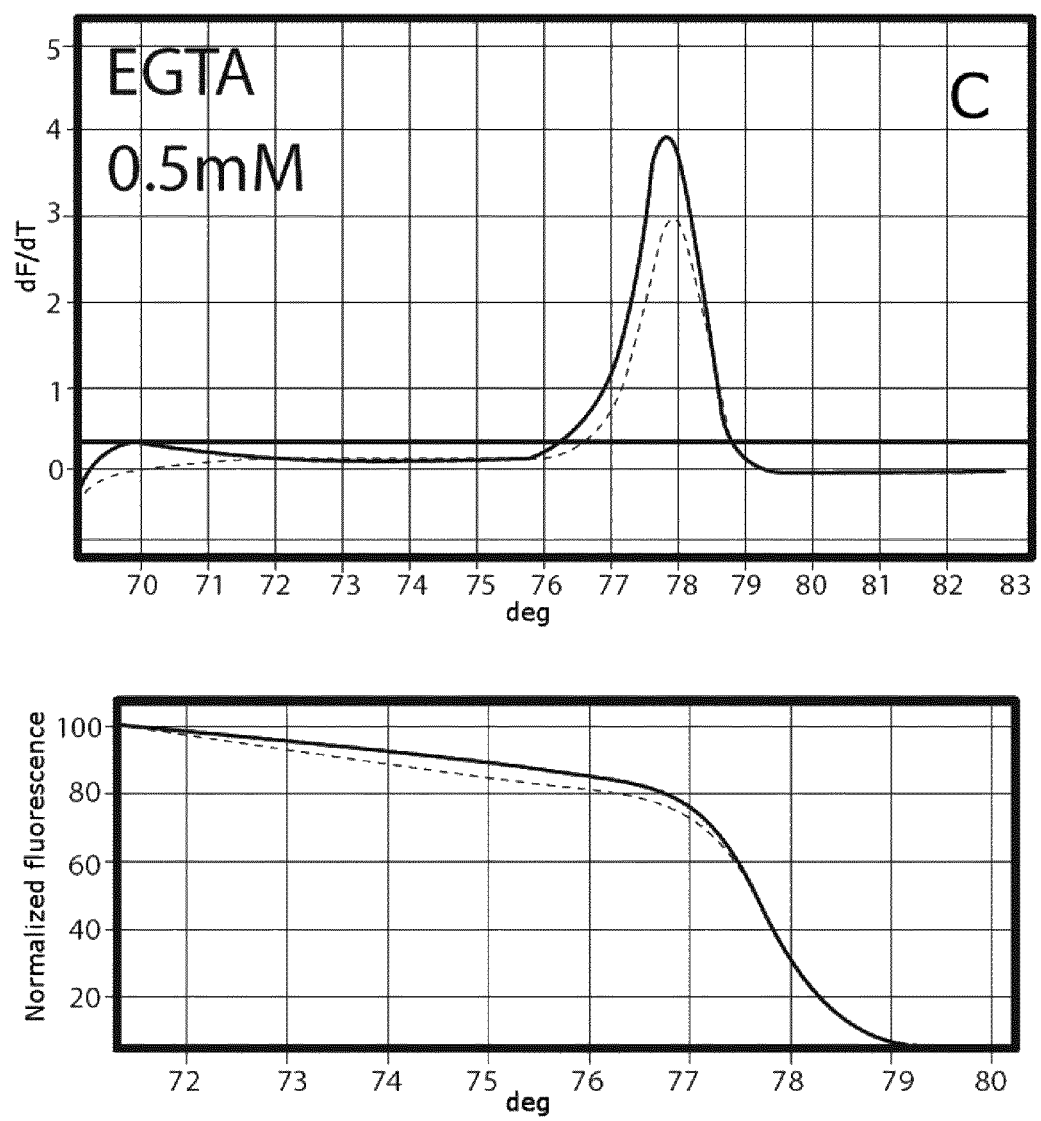
Figure 3:
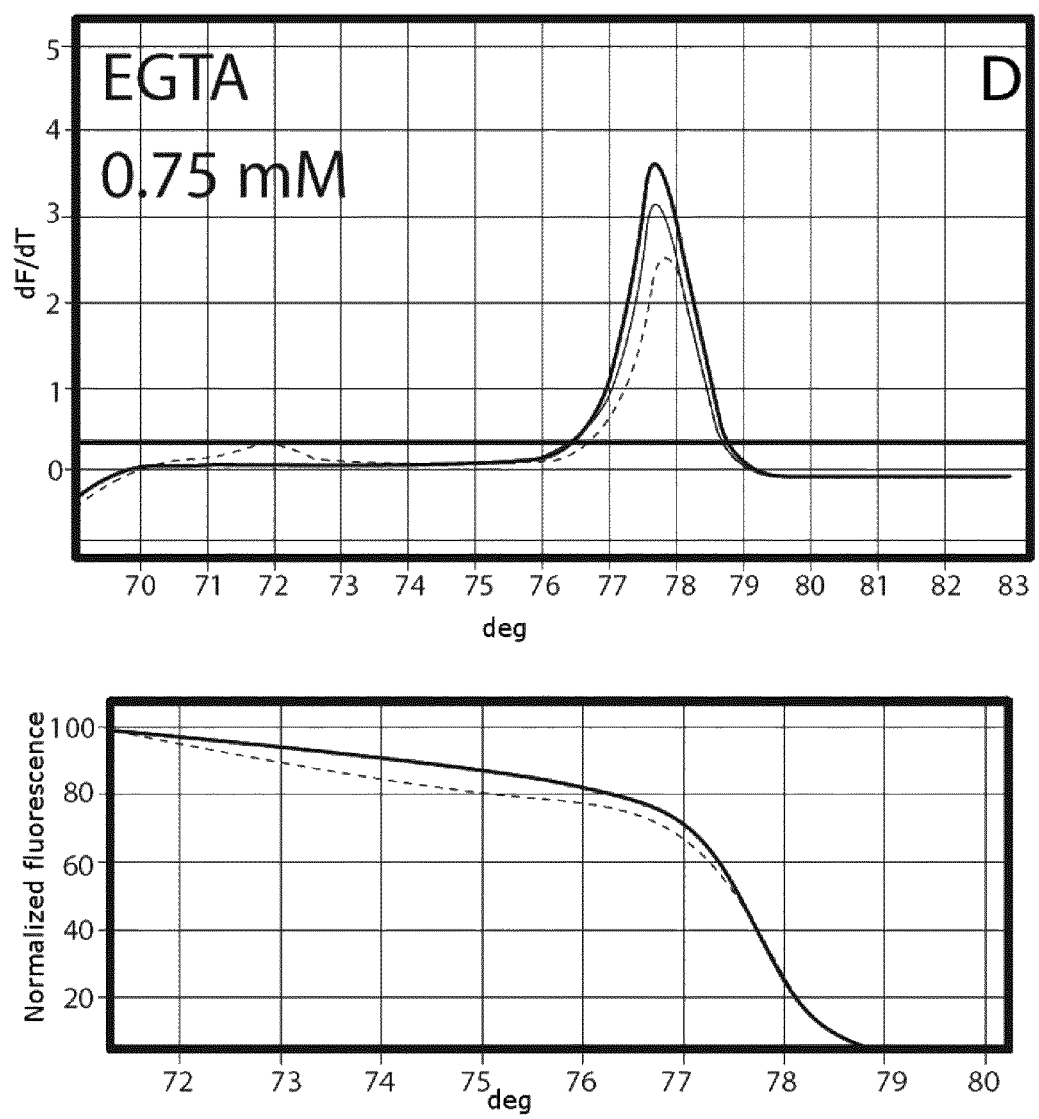
Figure 3:
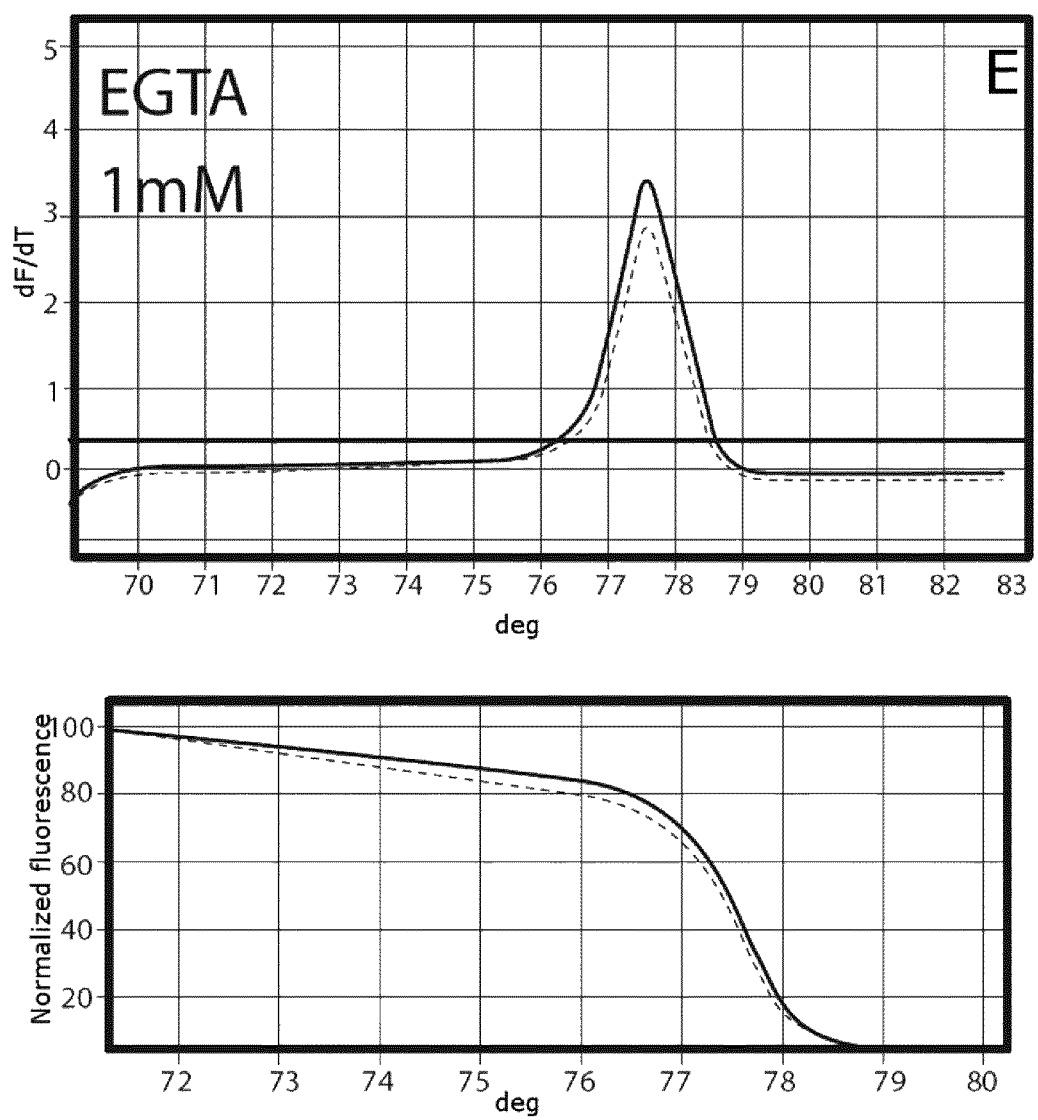
Figure 3:
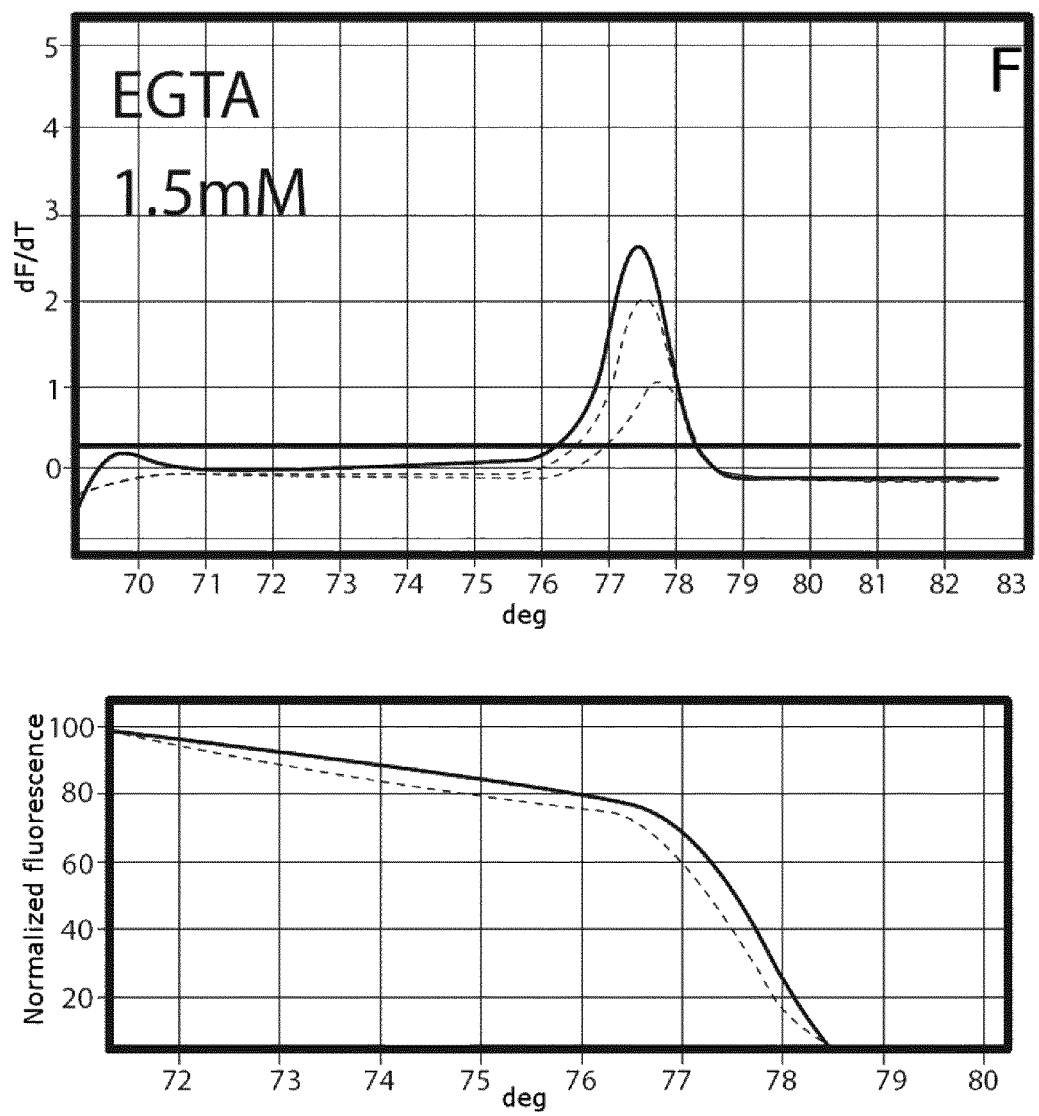
Figure 3:
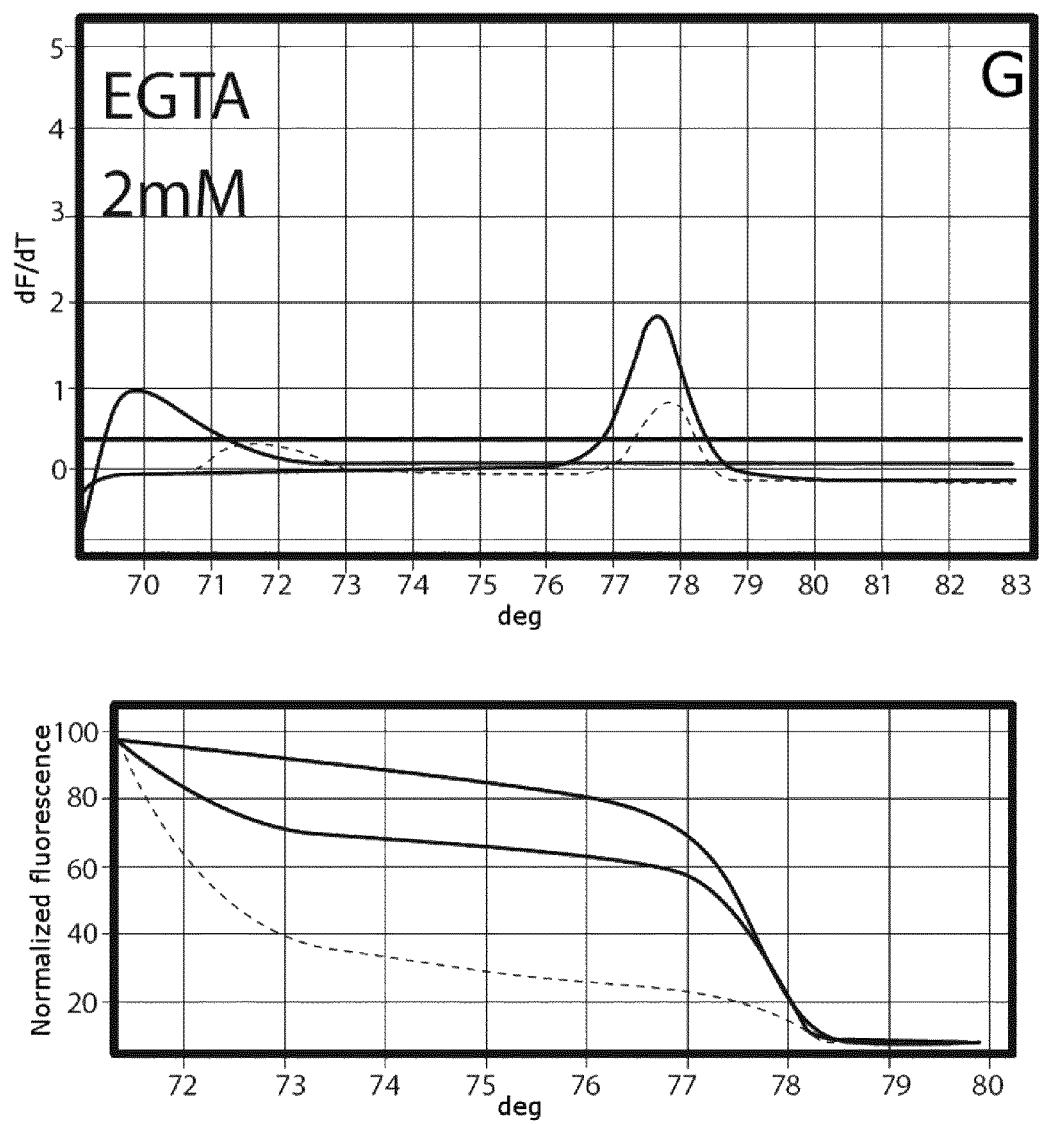
Figure 3:
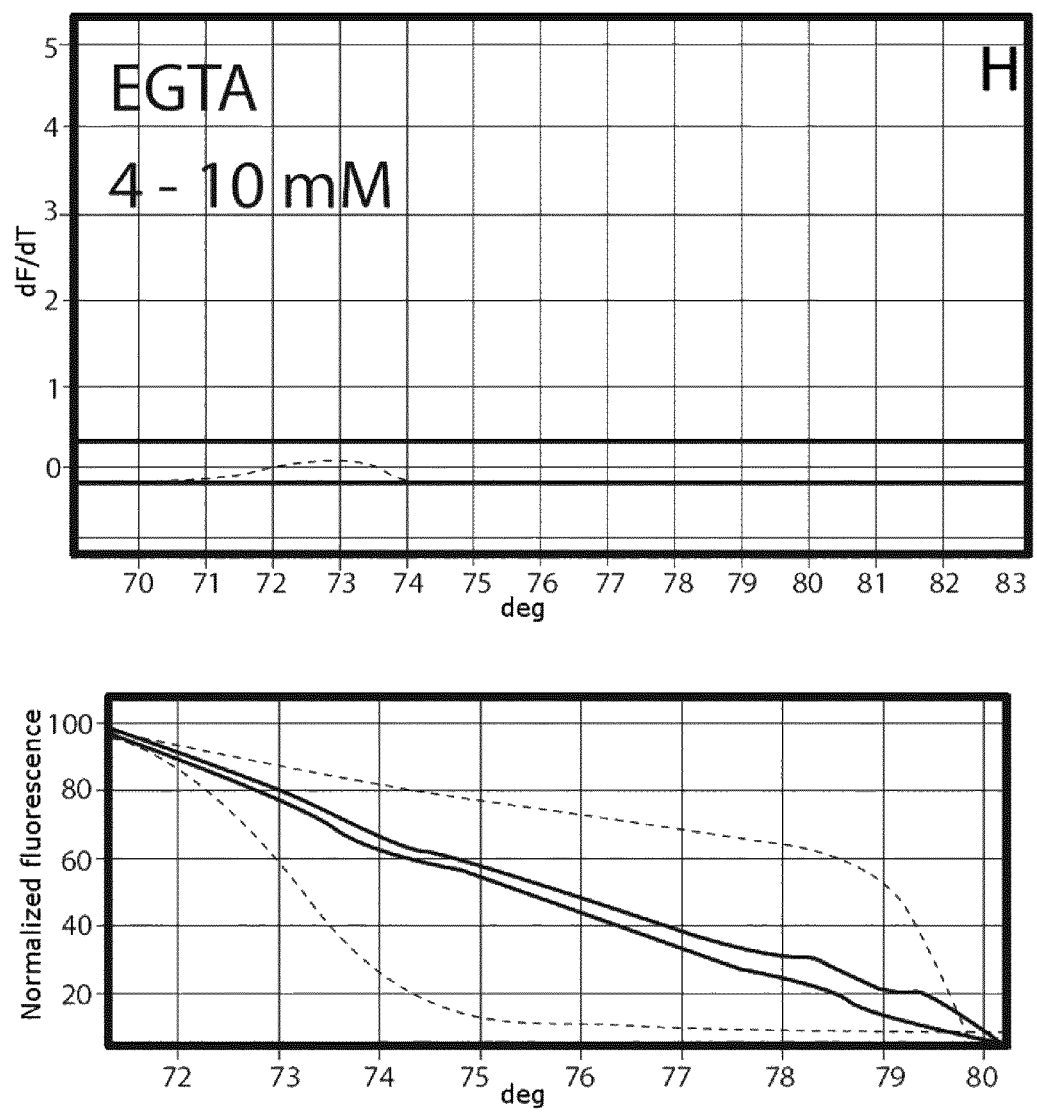

Ct values are summarized in Table 8 and FIG. 3 shows the respective melting curves.

TABLE 8

Summary of results obtained from the amplification experiment of bisulphite-treated DNA in the presence of different EGTA concentrations.

| | Room temperature | | | On ice | | |
|---|---|---|---|---|---|---|
| EGTA [mM] | Ct | Average | Standard deviaton | Ct | Average | Standard deviation |
| — | 25.01 | 24.92 | 0.1 | 25.29 | 25.28 | 0.01 |
| | 24.82 | | | 25.26 | | |
| 0.25 | 25.2 | 25.31 | 0.11 | 25.34 | 25.43 | 0.09 |
| | 25.42 | | | 25.51 | | |
| 0.5 | 25.55 | 25.51 | 0.04 | 25.53 | 25.58 | 0.04 |
| | 25.47 | | | 25.62 | | |
| 0.75 | 25.91 | 25.86 | 0.05 | 25.78 | 25.83 | 0.05 |
| | 25.8 | | | 25.88 | | |
| 1 | 26.47 | 26.49 | 0.02 | 26.59 | 26.55 | 0.04 |
| | 26.5 | | | 26.61 | | |
| 1.5 | 27.76 | 27.82 | 0.06 | 28.17 | 28.19 | 0.02 |
| | 27.88 | | | 28.21 | | |
| 2 | 29.9 | 29.81 | 0.09 | 30.16 | 29.35 | 0.82 |
| | 29.71 | | | 28.53 | | |
| 4 | 37.32 | 37.13 | 0.1 | 38.37 | 38.26 | 0.11 |
| | 37.02 | | | 38.14 | | |
| 8 | | | | | | |
| 10 | 35.18 | 34.59 | 0.59 | | | |
| | 34 | | | | | |

Samples that had been incubated on ice without the addition of EGTA showed a Ct value of 25.28 and a specific melting curve (FIG. 3A) whereas the Ct value in the case of the samples that had been incubated at room temperate is shifted to the right (24.92). In this case no specific product was observed. Addition of EGTA up to a final concentration of 0.75 mM resulted in an increase of specificity without affecting the Ct values. The amount of specific product increased rapidly. In the case of EGTA concentrations exceeded 2 mM, successful amplification was prevented (FIG. 3H).

In the follow-up experiment said primers and said bisulphite-treated DNA were used in amplification reactions wherein the magnesium dependency was analyzed. The composition of the reaction mixtures is shown in Table 9.

TABLE 9

Amplification reaction mixture.

| Reagent | Concentration | Volume (μl) |
|---|---|---|
| EpiTect HRM PCR Kit | 2x | 12.5 |
| Primer 1 | 10 μM | 1.875 |

TABLE 9-continued

Amplification reaction mixture.

| Reagent | Concentration | Volume (μl) |
|---|---|---|
| Primer 2 | 10 μM | 1.875 |
| Bisulphite-treated DNA | 10 ng/μl | 1 |
| Water or EGTA | 5 mM | 2.5 |
| Magnesium | 0.1 mM-0.6 mM | 2.5 |
| Water | | 2.75 |

The final concentration of EGTA was 5 mM. The HRM master mix was supplemented with 0.1 0.6 mM magnesium.

Two sets of reactions consisting of duplicates were used in the amplification experiment. One set of samples was incubated on ice for 120 min, whereas the other set of samples was incubated at room temperature for 120 min. Subsequently the samples were analyzed using the Rotor-Gene Q 5plex HRM System. The cycling program was the same as shown in Table 6. The results are shown in Table 9 and FIG. 4. Ct values corresponding to the samples incubated at room temperature and on ice respectively are shown in Table 10. FIG. 4 shows the respective melting curves.

TABLE 10

Summary of results obtained from the amplification experiment of bisulphite-treated DNA in the presence of EGTA and different magnesium concentrations.

| DNA | EGTA | MgCl$_2$ [mM] | Room temperature | | | On ice | | |
|---|---|---|---|---|---|---|---|---|
| | | | Ct | Average | Standard deviation | Ct | Average | Standard deviation |
| 10 ng | — | — | 22.41 | 22.62 | 0.21 | 25.32 | 25.46 | 0.14 |
| | | | 22.82 | | | 25.59 | | |
| | 5 mM | 0 mM | 28.86 | 28.77 | 0.09 | 28.74 | 28.82 | 0.08 |
| | | | 28.67 | | | 28.89 | | |
| | | 0.1 | 27.53 | 27.62 | 0.09 | 27.82 | 27.81 | 0.02 |
| | | | 27.71 | | | 27.79 | | |
| | | 0.2 | 26.69 | 26.98 | 0.29 | 26.85 | 27.12 | 0.27 |
| | | | 27.27 | | | 27.39 | | |
| | | 0.3 | 26.14 | 26.39 | 0.25 | 26.25 | 26.38 | 0.13 |
| | | | 26.64 | | | 26.51 | | |
| | | 0.4 | 26.06 | 26.15 | 0.09 | 26.01 | 26.08 | 0.06 |
| | | | 26.24 | | | 26.14 | | |
| | | 0.5 | 25.82 | 25.84 | 0.02 | 25.81 | 25.85 | 0.04 |
| | | | 25.86 | | | 25.89 | | |
| | | 0.6 | 25.55 | 25.52 | 0.03 | 25.61 | 25.59 | 0.03 |
| | | | 25.49 | | | 25.56 | | |

The experiment showed that in the case of the samples incubated on ice without the addition of EGTA a Ct value of 25.46 and a specific melting curve was obtained, whereas incubation at room temperature resulted in a shift of the Ct value (22.62) and no specific amplification product was observed. Addition of EGTA up to a final concentration of 5 mM led to increased specificity. The Ct value when using 5 mM EGTA was 28.77 and 28.82 respectively. Increasing the magnesium concentration resulted in lower Ct values whilst maintaining specificity.

Modulation of DNase Activity

In this set of experiments means of modulating activity of DNase, a nuclease isolated from bovine pancreas, were investigated.

Figure 5:
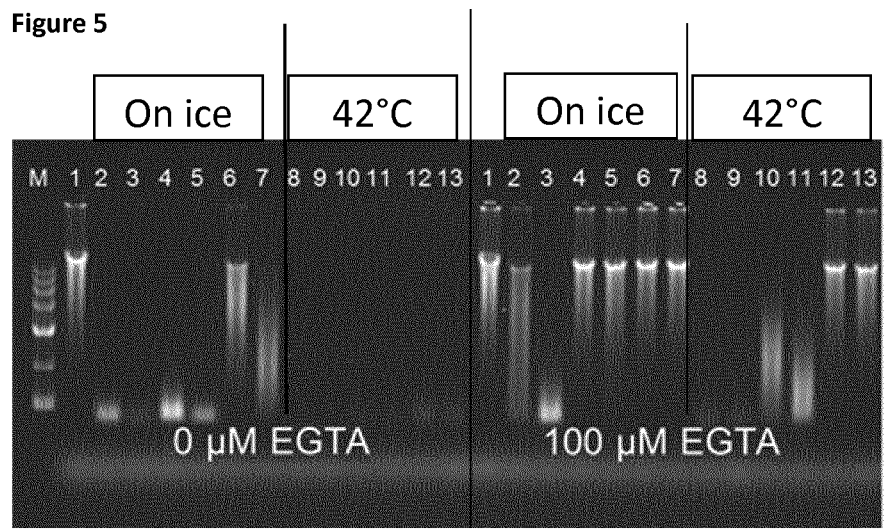

Human genomic DNA was propagated using the REPLI g Midi Kit (Qiagen) according to the manufacturer's instructions. DNase activity was analyzed in 10 µl reactions. Each reaction contained 50 mM Tris pH 8.2 as the reaction buffer, ~1 µg genomic DNA, 1 mM MgCl$_2$, and 50 µM CaCl$_2$. Three different amounts of DNase (0.01, 0.1 and 1 U) were used. The samples were incubated at two different temperatures, 42° C. and on ice, for 5 and 15 min respectively. DNA degradation was terminated by adding EDTA to a final concentration of 8.33 mM and samples were incubated on ice prior to analysis of the reaction products using a 0.5% agarose gel. The results are shown in FIG. 5. The gel shows that DNase is active on ice. Reaction time and the amount of DNase strongly influence completeness of enzymatic digestion. Incubation of said genomic DNA on ice for 15 min using 1 U DNase led to complete degradation of the sample (lane 3). Incubation at 42° C. led to complete degradation when using any of the amounts of enzyme already after 5 min (lanes 8-13, '42° C.').

Addition of EGTA to a final concentration of 100 µM led to almost complete inhibition of degradation for any of the amounts of DNase that were used (lanes 2-7, 'on ice' '100 µM EGTA'). Exempt from this is the reaction using 1 U DNase for 15 min (lane 3 'on ice' '100 µM EGTA'). However, in this case degradation is significantly reduced compared to the sample without EGTA. Increasing the temperature to 42° C. largely restored DNase activity (lanes 8-13 '42° C.' '100 µM EGTA').

In the follow-up experiment EDTA was used as a chelating agent. The procedure of genomic DNA propagation as well the buffer and reaction conditions were equivalent to the experiment as described above.

Figure 6:
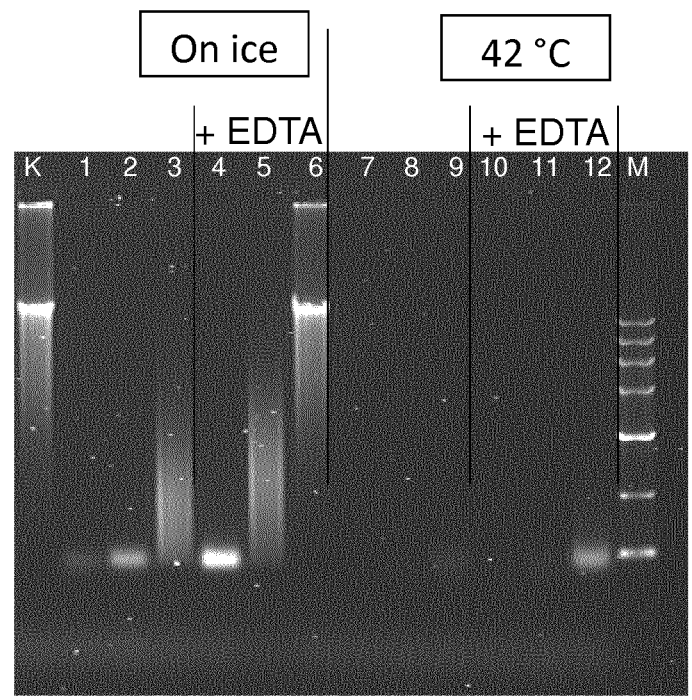

The reaction products were analyzed using a 0.5% agarose gel (FIG. 6). Lanes 1-6 correspond to samples where the reaction was performed on ice. A comparison of lanes 1-3 and lanes 4-6 shows that addition of EDTA largely reduced enzymatic activity. An increase in reaction temperature to 42° C. results in bound $Ca^{2+}$ ions being released from complexes with EDTA and thereby restoring enzymatic activity. Complete DNA degradation can be observed in lanes 7-12.

In summary, both examples show that chelating agents can be used to inhibit DNase activity and that shifting the reaction temperature restores enzymatic activity, thereby validating said system of activity regulation.

FIGURE CAPTIONS

FIG. 1: Selection of chelating agents. pH-dependency of pK values of EDTA, EGTA and NTA. Logarithmic values of the pK value was plotted versus the pH value.

Figure 2:
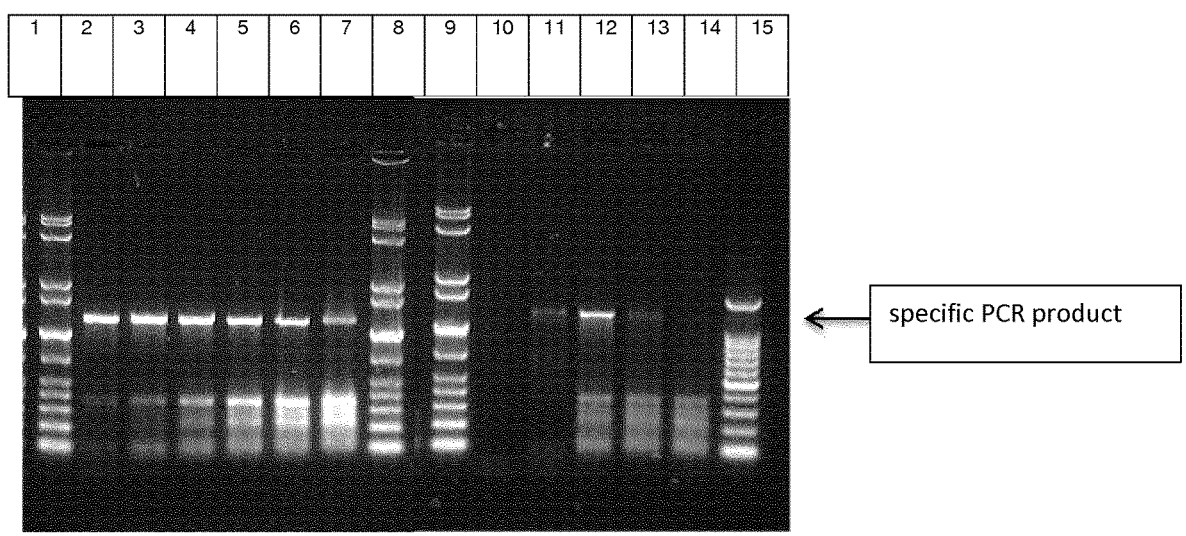

FIG. 2: Agarose gel of Hug1 PCR amplification experiment. The lanes are annotated as follows: 1: DNA ladder, 2: MMA +5 mM Mg, 3: MMA +6 mM Mg, 4: MMA +7 mM Mg, 5: MMA +8 mM Mg, 6: MMA +9 mM Mg, 7: MMA +10 mM Mg, 8: DNA ladder, 9: DNA ladder, 10: MMB +0.5 mM Mg, 11: MMB +1 mM Mg, 12: MMB +2 mM Mg, 13: MMB +3 mM Mg, 14: MMB +4 mM Mg, 15: DNA ladder.

An increase in Mg concentration leads to successful amplification of the target product 'specific PCR product', although much unspecific product is visible (lane 10-lane 12). A further increase of Mg concentration leads to generation of unspecific PCR products (lane 14, 4 mM Mg Cl$_2$). In contrast, addition of 5 mM EGTA in presence of 5-10 mM MgCl$_2$ results in specific PCR product (lane 2-lane 7), although the amount of unspecific by product increase while Mg concentration is increased.

FIG. 3

Melting curves (EGTA titration experiment).

The curves are annotated as follows: A: no additive, B: 0.25 mM EGTA, C: 0.5 mM EGTA, D: 0.75 mM EGTA, E: 1 mM EGTA, F: 1.5 mM, G: 2 mM EGTA, H: 4-10 mM.

FIG. 4

Melting curves (Mg titration experiment).

The curves are annotated as follows: A: no additives, B: 5 mM EGTA, C: 5 mM EGTA+0, 1 mM Mg, D: 5 mM EGTA+0.2 mM Mg, E: 5 mM EGTA+0.3 mM Mg, F: 5 mM EGTA+0.4 mM Mg, G: 5 mM EGTA+0.5 mM Mg, H: 5 mM EGTA +0.6 mM Mg.

FIG. 5

Agarose gel analysis of DNase assay at different temperatures and influence of EGTA.

Lanes are annotated as follows: Note that reactions corresponding to samples in lane 2-7 were performed on ice and are hence labelled 'on ice'. Similarly, reactions corresponding to samples in lanes 8-13 were performed at 42° C. and are labelled '42° C.' accordingly. Reactions at both temperatures were performed in the absence and presence of 100 µM EGTA CO µM EGTA and 100 µM EGTA respectively).

Lane M: GelPilot High Range Ladder (60), lane 1: 1 µg WGA gDNA (no DNase added), lanes 2 and 3: 1 µl DNase (1 U) 5 and 15 min, lanes 4 and 5: 0.1 µl DNase (0.1 U) 5 and 15 min, lanes 6 and 7: 0.01 µl DNase (0.01 U), 5 and 15 min, lanes 8 and 9: 1 µl DNase (1 U) 5 and 15 min, lanes 10 and 11: 0.1 µl DNase (0.1 U) 5 and 15 min, lanes 12 and 13: 0.01 µl DNase (0.01 U) 5 and 15 min.

FIG. 6

Agarose gel analysis of DNase assay at different temperatures and influence of EDTA.

Reactions corresponding to samples in lanes 1-6 were performed on ice and are hence labeled 'on ice' Reactions corresponding to samples in lane 7-12 were performed at 42° C. and are labeled '42° C.' accordingly. Lanes are annotated as follows: Lane K: 1 µg WGA gDNA.

Lane 1: 1 U DNase, lane 2: 0.5 U DNase, lane 3: 0.1 U DNase, Lane 4: 1 U DNase +100 µM EDTA, lane 5: 0.5 U DNase +100 µM EDTA, lane 6: 0.1 U DNase +100 µM EDTA.

Lane 7: 1 U DNase, lane 8: 0.5 U DNase, lane 9: 0.1 U DNase, lane 10: 1 U DNase +100 µM EDTA, lane 11: 0.5 U DNase +100 µM EDTA, lane 12: 0.1 U DNase +100 µM EDTA, lane M: GelPilot 1 kb Ladder (3 µl).

The invention claimed is:

1. A method for regulation of a nucleic acid modifying enzyme activity in a reaction composition, comprising:
   providing a reaction composition comprising:
   a. at least one nucleic acid modifying enzyme, wherein enzymatic activity of said enzyme depends on presence of divalent cations in the reaction composition and wherein the nucleic acid modifying enzyme is selected from:
      (1) a nucleic acid polymerase from an organism of genus *Thermus, Aquifex, Thermotoga, Thermocridis, Hydrogenobacter, Thermosynchecoccus, Thermoanaerobacter, Pyrococcales, Thermococcus, Radius,* or *Sulfolobus*; and
      (2) a nucleic acid polymerase from an organism selected from *Aquifex aeolicus, Aquifex pyogenes, Thermus thermophilus, Thermus aquaticus, Thermotoga neopolitana, Thermus pacificus, Thermus eggertssonii* and *Thermotoga maritima;*
   b. one or a plurality of divalent cations,
   c. a chelating agent of binding constant pK to which said divalent cation reversibly binds to form a complex, wherein binding of said divalent cation to the chelating agent is dependent on pH of the reaction composition and wherein the chelating agent has a log pK value of greater than 1.2 at pH 7.2,
   d. a buffering system having an acid dissociation constant that is temperature dependent, such that an increase in temperature in the reaction composition results in a lower pH of the reaction composition, and
   e. a substrate for said enzyme which comprises a nucleic acid target sequence; and
   (ii) amplifying the substrate for said enzyme in a temperature cycling amplification reaction which comprises a plurality of cycles of reversibly changing the temperature in the reaction composition to cause a reversible pH change in the reaction composition, such that the divalent cations which are reversibly bound to the chelating agent are released from the complex, wherein the enzyme is thereby activated or enzymatic activity of the enzyme is increased relative to the activity prior to said step of changing the temperature, and wherein the nucleic avid target sequence is specifically amplified to obtain a specific amplification product at a level that is greater than the level of the specific amplification product that is obtained when the chelating agent is not present.

2. The method of claim 1, wherein the enzymatic activity of said nucleic acid modifying enzyme comprises substrate binding and substrate processing.

3. The method of claim 1, wherein prior to changing the temperature, binding of the divalent cation to the chelating agent causes removal of said divalent cation from the nucleic acid modifying enzyme and results in decreased enzymatic activity or loss of enzymatic activity.

4. The method of claim 1, wherein the chelating agent is selected from the group consisting of ethylene diamine tetraacetate (EDTA), ethylene glycol bis(amino ethyl) N, N'-tetraacetate (EGTA) and nitrilotriacetate (NTA).

5. The method of claim 1, wherein the divalent cation is selected from the group consisting of $Mg^{2+}$, $Ca^{2+}$, $Mn^{2+}$, $Cu^{2+}$, $Fe^{2+}$, $Ni^{2+}$, $Zn^{2+}$ and $Co^{2+}$.

6. The method of claim 1, wherein the chelating agent is EDTA and the divalent cation is selected from $Mg^{2+}$, $Ca^{2+}$, $Mn^{2+}$, $Cu^{2+}$, $Ni^{2+}$, $Zn^{2+}$ and $Co^{2+}$.

7. The method of claim 1, wherein the chelating agent is EGTA and the divalent cation is either or both of $Ca^{2+}$ and $Mg^{2+}$.

8. The method of claim 1, wherein the chelating agent is NTA and the divalent cations are one or more of $Ca^{2+}$, $Cu^{2+}$ and $Co^{2+}$.

9. The method of claim 1, wherein one or more of:
   the reaction composition comprises a Tris buffer system;
   (ii) the divalent cation is $Mg^{2+}$ at a concentration between 0.01 and 20 mM;
   (iii) the chelating agent is EGTA at a concentration between 0.05 and 50 mM; and
   (iv) the nucleic acid modifying enzyme is a DNA polymerase.

10. The method of claim 1, wherein one or more of:
    (i) the reaction composition comprises a Tris buffer system;
    (ii) the divalent cation is selected from the group consisting of $Mg^{2+}$, $Ca^{2+}$, $Mn^{2+}$, $Cu^{2+}$, $Fe^{2+}$, $Ni^{2+}$, $Zn^{2+}$ and $Co^{2+}$; and
    (iii) the chelating agent is selected from EGTA, EDTA and NTA.

11. The method of claim 9 wherein the DNA polymerase is a hot start polymerase.

* * * * *

UNITED STATES PATENT AND TRADEMARK OFFICE
CERTIFICATE OF CORRECTION

PATENT NO. : 10,633,697 B2  
APPLICATION NO. : 15/114787  
DATED : April 28, 2020  
INVENTOR(S) : Alexander Azzawi et al.

Page 1 of 1

It is certified that error appears in the above-identified patent and that said Letters Patent is hereby corrected as shown below:

On the Title Page

Item (54):
"(54) CAUTION CHELATOR HOT START" should read: --(54) CATION CHELATOR HOT START--.

In the Claims

Column 17, Claim 1, Line 4:
"providing a reaction" should read: --(i) providing a reaction--.

Column 17, Claim 1, Lines 13-14:
"*Thermococcus, Radius, or Sulfolobus; and*" should read: --*Thermococcus, or Sulfolobus; and*--.

Column 17, Claim 1, Line 44:
"nucleic avid" should read: --nucleic acid--.

Signed and Sealed this  
Eighteenth Day of August, 2020

Andrei Iancu  
*Director of the United States Patent and Trademark Office*